United States Patent
Frazatti Gallina

(10) Patent No.: US 10,004,795 B2
(45) Date of Patent: Jun. 26, 2018

(54) PROCESS FOR PREPARING AN ATTENUATED TETRAVALENT DENGUE VACCINE

(71) Applicant: Fundacao Butantan, Sao Paulo (BR)

(72) Inventor: Neuza Maria Frazatti Gallina, Sao Paulo (BR)

(73) Assignee: Fundacao Butantan, Sao Paulo (BR)

( * ) Notice: Subject to any disclaimer, the term of this patent is extended or adjusted under 35 U.S.C. 154(b) by 0 days. days.

(21) Appl. No.: 14/847,422

(22) Filed: Sep. 8, 2015

(65) Prior Publication Data

US 2017/0065701 A1 Mar. 9, 2017

(51) Int. Cl.
| | |
|---|---|
| *A61K 39/00* | (2006.01) |
| *A61K 39/12* | (2006.01) |
| *C07K 14/00* | (2006.01) |
| *A61K 39/09* | (2006.01) |
| *C12N 7/00* | (2006.01) |
| *A61K 9/19* | (2006.01) |
| *B65B 3/00* | (2006.01) |

(52) U.S. Cl.
CPC ............... *A61K 39/12* (2013.01); *A61K 9/19* (2013.01); *B65B 3/003* (2013.01); *C12N 7/00* (2013.01); *A61K 2039/5254* (2013.01); *A61K 2039/70* (2013.01); *C12N 2770/24134* (2013.01); *C12N 2770/24151* (2013.01); *C12N 2770/24164* (2013.01)

(58) Field of Classification Search
CPC ............ A61K 39/12; A61K 2039/5254; C12N 2770/24134; C12N 7/00; C07K 14/005
See application file for complete search history.

(56) References Cited

U.S. PATENT DOCUMENTS 7,718,359 B2 * 5/2010 Guy .................. A61K 39/12
424/218.1
8,142,795 B2 * 3/2012 Francon ................. C12N 7/00
424/218.1

FOREIGN PATENT DOCUMENTS

WO WO2015048744 * 4/2015

OTHER PUBLICATIONS

Frazatti, Vaccine, 2004, 23:511-517.*
ATCC Vero (ATCC® CCL-81™), © ATCC 2014 product sheet, pdf pp. 1-2.*
Blaney et al., Development of a Live Attenuated Dengue Virus Vaccine Using Reverse Genetics, 2006, Viral Immunology, 19(1):10-32.*

* cited by examiner

*Primary Examiner* — Barry A Chestnut
(74) *Attorney, Agent, or Firm* — Finnegan, Henderson, Farabow, Garrett & Dunner, LLP

(57) ABSTRACT

The present invention refers to a process for preparing an attenuated tetravalent dengue vaccine and its product. The present invention also refers to a process for preparing a tetravalent dengue vaccine for administration to a subject, to a method for inducing an immune response to virus dengue serotype 1, 2, 3 and 4 in a patient and to a tetravalent dengue vaccine kit.

19 Claims, 1 Drawing Sheet

FLOW DIAGRAM OF DENGUE VACCINE 1,2,3,4 (ATENUATTED) PRODUCTION

Strains from NIH:
rDEN1Δ30-1545(03JB186)
rDEN2/4Δ30 (ME)-1495,7163(04JBV351)
rDEN3Δ30/31-7164(06JBC577)
rDEN4Δ30-7132,7163,8308(06JBV591)

Seed Virus Banks:
SVB/DEN1Δ30, SVB/DEN2/4Δ30,
SVB/DEN3Δ30/31 and SVB/DEN4Δ30

Working Seed Dengue Banks (DEN1Δ30, DEN2/4Δ30, DEN3Δ30/31 and DEN4Δ30

Vero cell (ATCC CCL-81.4) p. 123, qualified

Vero cell adaptation to serum-free medium

Vero Cell Master Bank

Vero Cell Working Bank

Vero cell in TC-flasks or Cell Factory System

Infection the Vero Cells with dengue virus from BVT banks

Incubation at 36.5°C

Harvests of Supernatants and Filtration

Bulks of dengue virus 1, 2, 3 and 4

Sterility
Virus Titration
Mycoplasma
Adventitious Agents in cells
Virus Identity
Haemadsorbing viruses Monovalent vaccines formulations
DEN1Δ30, DEN2/4Δ30, DEN3Δ30/31 and DEN4Δ30 monovalent Tetravalent vaccine formulation Filtration (0.22μm)

Sterility
Bacterial Endotoxin
Virus Titration
Virus Identity
pH
Aspect

Filling 3 ml/vial

Lyophilization

Sealing and Labeling

Sterility
Bacterial Endotoxin
Mycoplasma
Virus Titration
Virus Identity
pH
Aspect before and after reconstitution
Residual DNA Cellular
Residual Moisture Dengue vaccine 1,2,3,4 (attenuated)
Lyophilized with 10 doses/vial
$10^{3.2\pm0.5}$ PFU/serotype

PROCESS FOR PREPARING AN ATTENUATED TETRAVALENT DENGUE VACCINE

INCORPORATION OF SEQUENCE LISTING

The sequence listing that is contained in the file named "60135_146578_ST25.txt", which is 56,450 bytes (measured in operating system MS-Windows), created on Aug. 31, 2015, is filed herewith by electronic submission and incorporated herein by reference in its entirety.

FIELD OF THE INVENTION

The present invention is in the field of biotechnology. The present invention refers to a process for preparing an attenuated tetravalent dengue vaccine. The present invention also refers to an attenuated tetravalent dengue vaccine. The present invention also refers to the use of a composition for reconstituting the vaccine. The present invention also refers to a method for inducing an immune response to serotypes 1, 2, 3 and 4 in a patient. The present invention also refers to a tetravalent dengue vaccine kit.

BACKGROUND

Currently, dengue is a disease of major impact on public health in Brazil. It affects half of the world's population living in endemic regions, mainly in Southeast Asia (Pacific region) and America. According to the WHO, in the one recent study it was estimated that there are about 390 million dengue infections per year (95% credible interval 284-528 million), of which 96 million (67-136 million) manifest clinically (with any severity of disease) [1]. In another study about dengue prevalence, it was estimated that 3900 million people, in 128 countries, are at risk of infection with dengue virus [2].

In Brazil, in the year 2000 the incidence was 200,000 dengue cases and in 2010 there were a million occurrences. In 2015, there were 460,502 reported cases of dengue in Brazil until March. The Southeast region had the highest number of reported cases (304,251 cases, 66.1%) compared to the country, followed by the Midwest (59,855 cases; 13%), Northeast (51,221 cases; 11.1%), North (19,402 cases; 4.2%) and South (25 773 cases, 5.6% [3].

Dengue fever (DF) and its severe form, dengue hemorrhagic fever (DHF)/dengue shock syndrome (DSS) can be caused by infection with any of the dengue serotypes DEN1, DEN2, DEN3 and DEN4.

As currently there is no antiviral drug that treats this disease and the mosquito vector (*Aedes aegypti*) control strategies has proven ineffective, the only way to control the advance of dengue is through prevention, with the use of a vaccine against the four types of dengue virus. At the moment, no dengue vaccines have been licensed for human use. Epidemiological studies indicate that primary infection with one dengue serotype usually causes DF, and the chance of a second infection causes DHF is 15-80 times higher than that of primary infection. Therefore, an effective dengue vaccine must be composed of the four serotypes of virus dengue [4]. However, the development of a tetravalent dengue vaccine is very difficult because this product must provide a long-term protection against all dengue virus serotypes [5].

The U.S. patent application Ser. No. 13/305,639, continuation of application Ser. No. 12/398,043, filed on Mar. 4, 2009, now U.S. Pat. No. 8,075,903, which is a continuation of application Ser. No. 10/970,640, filed on Oct. 21, 2004, now U.S. Pat. No. 7,517,531, continuation of application no. PCT/US03/13279, filed on Apr. 25, 2003, from The Government of the USA, as represented by the Secretary, department of health and human services, is entitled "Dengue tetravalent vaccine containing a common 30 nucleotide deletion in the 3'-UTR of dengue types 1, 2, 3 and 4, or antigenic chimeric dengue viruses 1, 2, 3 and 4." The patent above refers to one product obtained from a process that include a mix of four dengue virus serotypes with a 30 nucleotide deletion or antigenic chimeric dengue virus.

The U.S. patent application Ser. No. 11/982,488, filed on Nov. 2, 2007, published on May 31, 2012 and granted on Aug. 14, 2012, from Monika Simmons et al, entitled "Induction of an immune response against dengue virus using the prime-boost approach", describes methods for the induction of an immune response to dengue virus. The method of inducing an immune response against dengue virus comprises administration of a non-replicating immunogen followed by a boost with a tetravalent live attenuated viral vaccine. Another aspect is a method of inducing an immune response against dengue virus using a heterologous prime-boost regimen with the priming immunogen comprising a DNA expression system, an adenovirus expression vector or a Venezuelan equine encephalitis virus replicon system and the boosting immunogen comprising the same without the DNA expression system. Each expression system contains DNA sequences encoding dengue viral proteins. The patent above describes an immune scheme for dengue vaccine. In this scheme the first immunization is used a non-replicating immunogen and after a tetravalent live attenuated dengue vaccine. The object of the present patent application is a process to obtain a live attenuated dengue vaccine.

The present invention teaches the development of a vaccine against the four types of dengue virus using the attenuated virus strains rDEN1Δ30-1545 (SEQ ID NO:1) and variants thereof; rDEN2/4Δ30(ME)-1495,7163 (SEQ ID NO:2) and variants thereof; rDEN3Δ30/31-7164 (SEQ ID NO:3) and variants thereof; and rDEN4Δ30-7132,7163, 8308 (SEQ ID NO:4) and variants thereof. Certain rDEN1Δ30, rDEN2/4Δ30, rDEN3Δ30, and rDEN4Δ30 recombinant attenuated dengue viruses are described in U.S. Pat. No. 7,517,531, U.S. Pat. No. 7,226,602 and U.S. Pat. No. 8,337,860, which are incorporated herein by reference in their entirety.

The vaccine of the present invention, called dengue vaccine 1, 2, 3, 4 (attenuated), is presented in lyophilized form in vials with 10 doses. In the development of this vaccine the following process was established: production of Vero cells and dengue virus of serotypes 1, 2, 3 and 4 to obtain the cell and virus banks; production of viral suspensions with cells and virus from these banks; concentration of these suspensions and preparation of bulks; formulation of monovalent and tetravalent vaccines; filling; lyophilization and sealing of the product.

As may be seen none of the prior art documents discloses or suggests a process for preparing an attenuated tetravalent dengue vaccine that enable dengue vaccine production on a large scale.

BRIEF SUMMARY OF INVENTION

In order to solve the problems above mentioned, the present disclosure will provide significant advantages over existing processes for preparing tetravalent dengue vaccines. Initially, certain embodiments of the present invention use Vero cell strains with lower passage (passage 123), which allows a high number of subcultures of this cell line, that is, a high yield. Moreover, Master and Working Vero cell banks were prepared with cells maintained in serum-free culture medium, were subcultured with a non-animal trypsin, and were stabilized with 5% DMSO. The use of a serum-free medium leads to higher reproducibility, not to mention that the use of non-animal trypsin in the subcultures of maintenance and amplification of Vero cells makes the process safer and free from the possibility of contamination of the final product with porcine circovirus. Moreover, Vero cells can be grown in 225 cm² TC-flasks (Tissue Culture Flasks) or Nunc™ Cell Factory System™, with 10-tray layers (Thermo Fisher Scientific Inc. Pittsburgh, Pa., USA; area of culture of about 6,320 cm²), which allows a high production of cells/TC-flask of up to about $2\times10^9$ cells/CFS. The additional replication of dengue virus in Vero cells, from which Working Virus Seed banks were prepared, increased the process' productivity. The final volume of viral suspension obtained in one production cycle with CFS is 14 L (a high volume). In certain embodiments of the present invention, up to about seven harvests can be obtained in a single production cycle of the virus. Dengue virus suspensions are harvested from the infected cells by removing of the media containing virus from the culture, replacing the removed media with fresh media, incubating the infected cells with the new media, and harvesting the media that contains virus after incubation, which also increases the productivity of the processes provided herein. The present disclosure also teaches the optimal time for harvesting supernatants of viral suspensions through studies of dengue virus replication curves of the serotypes 1, 2, 3 and 4 in Vero cells grown in TC-flasks and Cell Factory System™, which allows the increase in the number of harvestings. In certain embodiments, the tetravalent vaccine of the present disclosure is prepared with monovalent vaccines containing different titers of virus dengue according with each serotype (5.7±0.2, 5.6±0.2, 6.1±0.2 and 5.8±0.2 $Log_{10}$ PFU/ml for DENV1, DENV2, DENV3, and DENV4, respectively) which allows a higher homogeneity of viral particles of each serotype in the tetravalent vaccine. Finally, the steps of filling and lyophilization of the claimed process provide a vaccine that is stable for 1 year at 2-8° C.

In summary, the process for preparing an attenuated tetravalent dengue vaccine of the present application presents high yield and is very reproducible. The vaccine, product of said process, is highly stable and without contaminants of animal origin (serum and trypsin), generally used in the manufacturing of vaccines. Said characteristics allow the production of dengue vaccine on a large scale. In addition, the dengue vaccine of the present disclosure has been tested in humans in Brazil since November 2013 (phase II clinical trials). Preliminary data of this study demonstrated that this product is safe and immunogenic.

In one aspect, the present invention refers to process for preparing an attenuated tetravalent dengue vaccine characterized by the fact that it comprises any subset or all of the following steps: adapting Vero cells to growth in serum-free medium and using a trypsin non-animal origin to obtain the cells subcultures; amplifying Vero cells in 225 cm² TC-flasks and later in Cell Factory System™ (CFS); producing the Vero Cell Master Cell Bank (MCB) and Working Cell Bank (WCB) and the Seed Bank and Working Seed Bank with dengue's virus serotypes 1, 2, 3 and 4; infecting the Vero cells in 225 cm² TC-flasks or CFS from working cell bank with dengue's virus serotypes 1, 2, 3 and 4 from working seed virus banks; incubating the TC-flasks or Cell Factory System™ contained the Vero cells/virus dengue suspension at 36.5° C. (±1° C.) for 10 to 20 days; harvesting the supernatants, filtering (membrane of 0.2 µm of porosity) and storing at −80° C. (±5° C.); preparing bulks of dengue virus serotypes 1, 2, 3 and 4; formulating the monovalent vaccines with these bulks; formulating tetravalent vaccine with four monovalent vaccines; filling; lyophilizing; sealing; labeling and storing the product at 2-8° C.

In certain embodiments the Vero cell line used is ATCC CCL-81.4 (cGMPVero, Kidney African Green Monkey—*Cercopithecus aeothiops*). In a further embodiment the dengue virus strains used are rDEN1Δ30-1545; rDEN2/4Δ30(ME)-1495,7163; rDEN3Δ30/31-7164 and rDEN4Δ30-7132,7163,8308 from the United States National Institutes of Health (NIH). In a further embodiment the MOI of dengue virus strains for each dengue serotype can be about: 0.01 to 0.03 for DENV 1 and 4, 0.02 to 0.04 for DENV 2 and 0.05 to 0.08 for DENV3. In a further embodiment the monovalent vaccines are mixed in the same ratio of volume to obtain the tetravalent dengue vaccine serotypes 1, 2, 3, 4 (attenuated). In a further embodiment the parameters used in the freeze drying (lyophilization) process are: freezing (−30 to −50° C.), vacuum (20 to 100 µbar), primary drying from −30 to −50° C. (36 to 42 h) and −5 to −10° C. (18 to 24 h) secondary drying 25 to 29° C. (8 to 15 h).

In another aspect, the invention refers to an attenuated tetravalent dengue vaccine produced by the process as described above.

In another aspect, the invention refers to the use of a composition comprising sodium phosphate monobasic dihydrate 0.2 M, sodium phosphate dibasic heptahydrate, 0.2 M and WFI (i.e., water for injection) water for reconstituting the vaccine produced by the process as described above. In an embodiment it used 5 mL of said composition to reconstitute the dried vaccine.

In another aspect, the invention refers to a method for inducing an immune response to virus dengue serotypes 1, 2, 3 and 4 in a subject by administering the vaccine as cited above to the subject. In certain embodiments, the subject is a human.

In another aspect, the invention refers to a tetravalent dengue vaccine kit that comprises the lyophilized tetravalent vaccine as cited above, a reconstitution composition comprising sodium phosphate monobasic dihydrate 0.2 M, sodium phosphate dibasic heptahydrate, 0.2 M and WFI water.

In certain embodiments, processes for preparing an attenuated tetravalent dengue vaccine comprising: (i) amplifying Vero cells in culture to produce Master and Working banks of Vero cells, wherein the Vero cells are adapted for growth in serum-free medium, are grown in serum-free medium, and are sub-cultured with trypsin of non-animal origin of this cell in 225 cm2 Tissue Culture (TC)-flasks and later in a Cell Factory System™ (CFS); (ii) infecting Vero cells from the Master or Working bank with dengue virus serotypes 1, 2, 3 and 4 from a Seed or Working bank of each virus, wherein the Vero cells are independently infected with dengue virus serotypes 1, 2, 3, and 4 in separate cultures with serum free medium; (iii) incubating the 225 cm2 TC-flasks or Cell Factory System™ (CFS) containing the Vero cells infected with each dengue virus at 36.5° C. (±1° C.) for 10 to 20 days; (iv) harvesting the supernatants of each culture; (v) filtering each dengue virus suspension from step (iv) through a membrane with 0.2 µm of porosity and storing the filtered dengue virus at −80° C. (±5° C.); (vi) preparing dengue virus bulks of the serotypes 1, 2, 3 and 4; (vii) formulating monovalent vaccines; (viii) formulating tetravalent vaccine by mixing the monovalent vaccines; (ix) filling vials with the tetravalent vaccine; (x) lyophilizing the tetravalent vaccine in the vials; (xi) sealing the lyophilized tetravalent vaccine in the vials; and (xii) storing the lyophilized and sealed product at 2-8° C., thereby preparing an attenuated tetravalent dengue vaccine are provided.

In certain embodiments, a process for preparing an attenuated tetravalent dengue vaccine comprising: (i) amplifying Vero cells in culture to produce Master and Working banks of Vero cells, wherein the Vero cells are adapted for growth in serum-free medium, are grown in serum-free medium, and are sub-cultured with trypsin of non-animal origin; (ii) infecting Vero cells from the Master or Working bank with dengue virus serotypes 1, 2, 3 and 4 from a Seed or Working bank of each virus, wherein the Vero cells are independently infected with dengue virus serotypes 1, 2, 3, and 4 in separate cultures with serum free medium; (iii) incubating the Vero cells infected with each dengue virus at 36.5° C. (±1° C.) for 10 to days in a tissue culture flask or Cell Factory System™; (iv) harvesting the supernatants of each culture; (v) filtering each dengue virus suspension from step (iv) through a membrane with 0.2 µm of porosity and storing the filtered dengue virus at −80° C. (±5° C.); (vi) preparing dengue virus bulks of the serotypes 1, 2, 3 and 4; (vii) formulating monovalent vaccines; and (viii) formulating tetravalent vaccine by mixing the monovalent vaccines is provided.

In certain embodiments, an attenuated tetravalent dengue vaccine that is produced by any of the aforementioned processes is provided.

In certain embodiments, a process for preparing a tetravalent dengue vaccine for administration to a subject that comprises the step of reconstituting the sealed and lyophilized tetravalent dengue vaccine produced by any of the aforementioned methods in a composition comprising 0.2M sodium phosphate monobasic dihydrate, 0.2M sodium phosphate dibasic heptahydrate, and water is provided.

Also provided are methods for inducing an immune response to virus dengue serotypes 1, 2, 3 and 4 in a subject that comprise administering the aforementioned vaccine to the subject.

Also provided are tetravalent dengue vaccine kits that comprise the aforementioned vaccine, a reconstitution composition comprising 0.2M sodium phosphate monobasic dihydrate, 0.2M sodium phosphate dibasic heptahydrate and water.

In certain embodiments of any of the aforementioned processes, vaccines, methods, or kits, the dengue virus strains used are rDEN1Δ30-1545 (SEQ ID NO:1) or a variant thereof; rDEN2/4Δ30(ME)-1495,7163 (SEQ ID NO:2) or a variant thereof; rDEN3Δ30/31-7164 (SEQ ID NO:3) or a variant thereof, and rDEN4Δ30-7132,7163,8308 (SEQ ID NO:4) or a variant thereof.

BRIEF DESCRIPTION OF THE DRAWINGS

The purpose of the disclosure, together with further advantages thereof, can be better understood by reference to the accompanying drawing and the following descriptions:

FIG. 1 is a summary of the disclosure, describing all the steps of the process for preparing an attenuated tetravalent dengue vaccine.

DESCRIPTION

Although the present invention may be susceptible to different embodiments, certain embodiments are shown in the drawings and following detailed discussion, with the understanding that the present disclosure can be considered an exemplification of the principles of the invention and is not intended to limit the scope of invention to that which is illustrated and disclosed in this description.

A Process for Preparing an Attenuated Tetravalent Dengue Vaccine

In a first embodiment, the present invention refers to a process for preparing an attenuated tetravalent dengue vaccine comprising any subset or all of the following steps: adapting Vero cells to growth in serum-free medium and trypsin of non-animal origin; amplifying Vero cells in culture of this cell in 225 cm$^2$ TC-flasks and later in Cell Factory System™ (CFS); producing Master and Working banks of Vero cells and Seed and Working banks of dengue's virus serotypes 1, 2, 3 and 4; infecting Vero cells contained in 225 cm$^2$ TC-flasks or CFS with dengue's virus serotypes 1, 2, 3 and 4 from banks; incubating the 225 cm$^2$ TC-flasks or CFS containing the Vero cells/virus suspension infected with dengue virus at 36.5° C. (±1° C.) for 10 to 20 days; harvesting the supernatants of these cultures, filtering these dengue virus suspension in membrane with 0.2 µm of porosity and storing at −80° C. (±5° C.); preparing dengue virus bulks of serotypes 1, 2, 3 and 4; formulating monovalent vaccines with these bulks; formulating tetravalent vaccine mixing the monovalent vaccines; filling, lyophilizing; sealing and storing the product at 2-8° C. In a further embodiment the Vero cell line used is ATCC CCL-81.4 (cGMPVero, Kidney African Green Monkey—*Cercopithecus aeothiops*; available from the ATCC, Manassas, Va., USA). In a further embodiment the dengue virus strains used are rDEN1Δ30-1545 (SEQ ID NO:1) or variants thereof; rDEN2/4Δ30(ME)-1495,7163 (SEQ ID NO:2) or variants thereof; rDEN3Δ30/31-7164 (SEQ ID NO:3) or variants thereof; and rDEN4Δ30-7132,7163,8308 (SEQ ID NO:4) or variants thereof. Variants of the aforementioned dengue virus strains that can be used include but are not limited to: (1) variants of rDEN1Δ30-1545 (SEQ ID NO:1) having a genome with at least 95%, 96%, 97%, 98%, 99%, or 99.5% sequence identity across the entire length of SEQ ID NO:1 and variants with the aforementioned percent sequence identities that encode a viral polyprotein with at least 95%, 96%, 97%, 98%, 99%, or 100% sequence identity to the viral polyprotein encoded by SEQ ID NO:1; (2) variants of rDEN2/4Δ30(ME)-1495,7163 (SEQ ID NO:2) having a genome with at least 95%, 96%, 97%, 98%, 99%, or 99.5% sequence identity across the entire length of SEQ ID NO:2 and variants with the aforementioned percent sequence identities that encode a viral polyprotein with at least 95%, 96%, 97%, 98%, 99%, or 100% sequence identity to the viral polyprotein encoded by SEQ ID NO:2; (3) variants of rDEN3Δ30/31-7164 (SEQ ID NO:3) having a genome with at least 95%, 96%, 97%, 98%, 99%, or 99.5% sequence identity across the entire length of SEQ ID NO:3 and variants with the aforementioned percent sequence identities that encode a viral polyprotein with at least 95%, 96%, 97%, 98%, 99%, or 100% sequence identity to the viral polyprotein encoded by SEQ ID NO:3; and (4) variants of rDEN4Δ30-7132,7163,8308 (SEQ ID NO:4) having a genome with at least 95%, 96%, 97%, 98%, 99%, or 99.5% sequence identity across the entire length of SEQ ID NO:3 and variants with the aforementioned percent sequence identities that encode a viral polyprotein with at least 95%, 96%, 97%, 98%, 99%, or 100% sequence identity to the viral polyprotein encoded by SEQ ID NO:4.

rDEN1Δ30 (GenBank access number: AY145123) is a live attenuated virus derived from the DEN1 Western Pacific (WP) wild-type strain by means of a deletion of 30 nucleotides (Δ30) in the 3' untranslated region (3'UTR). The rDEN1Δ30-1545 strain (SEQ ID NO: 1) used herein encodes a single Lys→Arg mutation at amino acid residue number 484 (A1545G mutation) in the viral polyprotein.

For the development of the DEN2 virus, the ME region of DEN2 was substituted for the corresponding genes of rDEN4Δ30 to create the vaccine candidate rDEN2/4Δ30 (ME). The rDEN2/4Δ30(ME)-1495,7163 strain (SEQ ID NO: 2) used herein encodes a Ser→Phe mutation at amino acid residue number 186 (C1495T mutation) and a Leu→Phe mutation at amino acid residue number 112 (A7163C mutation) in the viral polyprotein.

rDEN3Δ30/31 is a live attenuated virus derived from rDEN3Δ30 strain. Initially it was constructed a complete cDNA copy of the strain DEN3 Sleman/78, creating a deletion of 30 nucleotides (Δ30) in the 3'UTR. As from the resulting rDEN3Δ30 virus, an additional deletion of about 31 nucleotides was carried out in the 3'UTR [2]. Therefore, rDEN3Δ30/31 includes the original Δ30 deletion and a non-contiguous 31 nt deletion that removes both the original TL-2 and TL-3 structures. The resultant rDEN3Δ30/31-7164 strain (SEQ ID NO: 3) used herein encodes a Val→Ala mutation at amino acid residue number 115 (T7164C mutation) in the viral polyprotein.

rDEN4Δ30 is a live attenuated virus derived from the wild-type DEN4 Dominica/81 using recombinant DNA technology. One stem-loop structure, identified as TL2 in the secondary structure of the 3' UTR, was previously removed by deletion of 30 nucleotides from the DEN4 genome (3'd 172-143) and has subsequently been designated as Δ30 mutation. The rDEN4Δ30-7132, 7163, 8308 strain (SEQ ID NO: 4) used herein encodes a Thr→Ile mutation at amino acid residue number 102 (C7132T mutation), a Leu→Phe mutation at amino acid residue number 112 (A7163C mutation) and a Lys→Arg mutation at amino acid residue number 249 (A8308G mutation) in the viral polyprotein.

In a further embodiment the MOI of dengue virus strains varies for each dengue serotype: 0.01 to 0.03 for DENV 1 and 4, 0.02 to 0.04 for DENV 2 and 0.05 to 0.08 for DENV3. In a further embodiment the monovalent vaccines are mixed in the same ratio of volume to obtain the tetravalent dengue vaccine serotypes 1, 2, 3, 4 (attenuated). In a further embodiment the parameters used in the freeze drying process are: freezing (−30 to −50° C.), vacuum (20 to 100 μbar), drying from −30 to −50° C. (36 to 40 h), from −5 to −10° C. (18 to 24 h) and 25 to 29° C. (8 to 15 h). In certain embodiments, the adaptation of Vero cell to serum-free medium was carried out with passage 123; the working cell bank was carried out with passage 134; and, the process for production of dengue virus used Vero cells with passage 138 to 149.

In certain embodiments, a stabilizer is used before step (vii) of formulation of monovalent vaccines. Suitable stabilizers for certain embodiments of the present invention include, but are not limited to, trehalose, sucrose, maltose, lactose, galactose, ASO4 (an stabilizer system including a mixture of stable aluminum hydroxide and monophosphoryl lipid A), human serum albumin (HSA), Pluronic® block copolymers F127, F68 (BASF), P85 (BASF) and P123 (BASF), polysaccharide chitosan, and recombinant HSA (rHSA) [8, 9].

An Attenuated Tetravalent Dengue Vaccine

In another embodiment the present invention refers to an attenuated tetravalent dengue vaccine produced by the process as described above.

Use of a Composition for Reconstituting the Dried Vaccine

In another embodiment a composition comprising sodium phosphate monobasic dihydrate 0.2 M, sodium phosphate dibasic heptahydrate, 0.2 M and WFI water is used to reconstitute the vaccine as described above. In a further embodiment 5 mL of the composition is used to reconstitute the dried vaccine.

A Method for Inducing an Immune Response to Virus Dengue Serotypes 1, 2, 3 and 4 in a Patient In another embodiment the present invention refers to a method for inducing an immune response to virus dengue serotypes 1, 2, 3 and 4 in a subject by administering the vaccine as described above to the subject.

For prophylactic treatment against Dengue infection, it is intended that the vaccine of the present invention can be administered prior to exposure of an individual to Dengue virus serotypes 1-4 and that the resulting immune response can inhibit or reduce the severity of the Dengue infection.

A Tetravalent Dengue Vaccine Kit

In another embodiment the present invention refers to a tetravalent dengue vaccine kit comprising the vaccine as described above, a reconstitution composition comprising sodium phosphate monobasic dihydrate 0.2 M, sodium phosphate dibasic heptahydrate, 0.2 M and WFI water.

EXAMPLES

Example 1. Description of Production Process

The process of production of dengue vaccine 1, 2, 3, 4 (attenuated) comprises the following steps:

Step 1. Preparation of Culture Media and Solutions Used in the Process of Vaccine's Production The serum-free culture media for maintenance of Vero cells, preparation of Bulks and formulation of vaccine are prepared as follows:

VP-SFM AGT or AGT OptiPRO® (GIBCO) serum-free media: flask of powdered culture medium is diluted in WFI water, and thereto is added L-Glutamine so that, at the end, the culture medium present 200 mM of this reagent. The medium is sterilized by filtration in membrane of 0.2 μm and samples are taken for measurement of pH and Sterility test.

Leibovitz (L-15) culture media without phenol red: flasks containing the powdered culture medium are diluted in WFI water. Then, the medium is filtered in membrane of 0.2 μm. Samples are taken for sterility, bacterial endotoxin, pH and appearance testing.

The culture media filtered are packed in polycarbonate flasks and stored at 2-8° C.

Buffered saline solution with 0.02M Phosphate is composed of sodium chloride, dibasic sodium phosphate, monobasic potassium phosphate, and WFI water. This solution is used for washing the cultures during the amplification cell process and in the dengue virus suspensions concentration.

Step 2. Preparation of Banks of Master and Working Vero Cells

The Vero cell banks were obtained from adaptation of Vero cell line ATCC CCL-81.4 (e.g. cGMPVero, Kidney African Green Monkey—*Cercopithecus aeothiops* p. 123 Batch 7388125) to the culture in serum-free medium and non-animal origin trypsin. This adaptation was carried out by successive subculture of this cell in culture cell 225 cm² T-flasks for cell culture using the serum-free medium (VP-SFM AGT®—GIBCO) and recombinant trypsin (TrypLE Select®—Gibco). After adaptation of the cells that only grow in medium with serum for growth in serum-free medium, cultures grown in serum-free medium are used to prepare the cell banks.

In the preparation of Master and Working cell banks, adapted Vero cells contained in culture flasks with a confluence of 90 to 100% are detached with trypsin, suspended in medium OptiPRO AGT (Gibco), centrifuged and the pelleted is resuspended in the same medium containing 5% DMSO. The cell suspension is homogenized and distributed into cryotubes containing 4 to $10 \times 10^6$ cells/ml. The cryotubes are placed in a freezer at 80° C. (±5° C.), for 48 hours and then stored in liquid nitrogen. Samples are taken for bank certification through the following quality control tests: Sterility, Karyotyping, Cell Identity, Adventitious Agents in Cells and Animals, Hemadsorbents Virus and Mycoplasmas.

Step 3. Amplification of Vero Cells Used as Cellular Substrate in the Production of Dengue Virus The cell amplification process includes thawing of a cryotube containing Vero cells from an origin cell (ATCC-CCL81.4) or from master or working cell banks in a water bath at 37° C. (±1° C.). After thawing, the suspension of Vero cell is placed in T-flask with serum-free medium and incubated at 36.5° C. (±1° C.) until the coverage of the cell monolayer is 90 to 100% of the T-flask cultivation area. The flasks are removed from the incubator and the cells are submitted to a new subculture. In this process, the cell monolayer is washed with saline solution buffered with phosphate 0.02M and detached with recombinant trypsin (Tryple Select®—GIBCO). The cells are suspended in serum-free medium and split into TC-flasks containing the same medium. The TC-flasks are incubated again at 36.5° C. (±1° C.) until reaching a coverage of 90 to 100% and then further subcultured. Amplification of the cells is initially, made in 225 $cm^2$ TC-flasks and later in a Cell Factory System™ (CFS) with 10 tray layers.

Step 4. Preparation of Working Dengue Virus Banks DEN1, DEN2, DEN3 and DEN4

TC-flasks with 225 $cm^2$ of culture area containing amplified Vero cells are infected with the dengue virus strains rDEN1Δ30-1545 (SEQ ID NO:1); rDEN2/4Δ30(ME)-1495,7163 (SEQ ID NO:2); rDEN3Δ30/31-7164 (SEQ ID NO:3); and rDEN4Δ30-7132,7163,8308 (SEQ ID NO:4), separately. The MOI (Multiplicity of Infection) used for virus infection is different for each serotype: 0.01 to 0.03 for DENV 1 and DENV 4, 0.02 to 0.04 for DENV 2 and 0.05 to 0.08 for DENV3. The infected cultures are incubated at 36.5° C. (±1° C.). After 8 days of incubation, supernatants of the cultures infected with DEN1Δ30, DEN2/4Δ30(ME)-1495,7163, DEN3Δ30/31-7164 and DEN4Δ30-7132,7163,8308 are separately harvested, filtered through a sterilizing membrane and stored in a freezer at −80° C. (±5° C.). The culture medium of flasks is replaced, and the flasks are again incubated at 36.5° C. (±1° C.). This procedure is repeated for three consecutive days to produce at the end four samples of the supernatants. For cultures infected with DEN3, this procedure begins on the 10th day of incubation. Samples of each harvest of the cultures' supernatant are taken for sterility and virus titration tests.

In the preparation of working banks, harvests approved in sterility tests, with titers higher than $10^{5.0}$ PFU/ml are mixed, distributed into cryotubes with 2 to 4 mL and maintained in liquid nitrogen. The bank is used after being approved in the following tests: Viral Identity, Sterility, Titration, Adventitious Agents in Cells and Animals, Hemadsorbents Virus and Mycoplasmas.

Step 5. Production of Dengue Virus Serotypes 1, 2, 3 and 4 for Dengue Vaccine Formulation After amplification, Vero cells contained in TC-flasks or Cell Factory System™ obtained from the amplification process, as described in step 3, are trypsinized and suspended in serum-free medium (OptiPRO® AGT—GIBCO). The Vero cell suspension obtained is inoculated with dengue virus strains rDEN1Δ30-1545, rDEN2/4Δ30(ME)-1,495.7163, rDEN3Δ30/31-7164 and rDEN4Δ30-7132,7163,8308, from the banks of dengue virus prepared in step 4 of the process for production of dengue vaccine. For inoculation the different MOIs (Multiplicity of Infection) for each serotype are used: 0.01 to 0.03 for DENV 1 and DENV 4, 0.02 to 0.04 for DENV 2 and 0.05 to 0.08 for DENV3. After inoculation, the virus/cell suspension is stirred at 32° C. (±1° C.) for 30 to 60 minutes and then distributed in 225 $cm^2$ TC-flasks or CFS with 10 tray layers. Serum-free culture media is added to cultures until it reaches the volume of 100 to 150 mL in the TC-flask and 1,200 to 1,800 ml for CFS. For CFS with different numbers of tray layers, it is calculated that the volume of culture medium to be added by making a rule of three. The cultures are incubated at 36.5° C. (±1° C.). On the 8th or 10th day of incubation, 50% to 60% of the medium is removed, and the same volume of serum-free medium is added in the cultures. The cultures are incubated again at 36.5° C. (±1° C.). The harvest of the supernatants of infected Vero cell cultures occur from the 10th to the 20th day after inoculation of dengue virus.

The harvest process includes the removal of the supernatants of the TC-flasks or CFS cultures infected, mixture of the supernatants harvested, a sterilizing filtration of this mixture, distribution of the dengue virus suspension filtered in polypropylene/polycarbonate flasks and storage in a freezer at −80° C. (±5° C.). Samples are taken for Sterility and Viral Titration tests. After approbation in the tests, the flasks with the virus dengue suspension are removed from the freezer and forwarded to the concentration process.

The virus dengue suspension harvested are thawed and concentrated by tangential filtration process using a Pellicon® System (Millipore) with a membrane of 30 to 50 kDa of porosity. Samples are taken for control quality tests: Viral titration and Sterility. The viral concentrate (C1) of rDEN1Δ30-1545, rDEN2/4Δ30(ME)-1495,7163, rDEN3Δ30/31-7164, or rDEN4Δ30-7132,7163,8308 is denominated and stored at −80° C. (±5° C.).

Step 6. Preparation of Dengue Virus Bulks

Dengue virus concentrate C1 (rDEN1Δ30-1545, rDEN2/4Δ30(ME)-1495,7163, rDEN3Δ30/31-7164, or rDEN4Δ30-7132,7163,8308) are removed from the freezer at −80° C. (±5° C.), thawed and subjected to the following process: the virus concentrate is diluted with Leibovitz medium without phenol red and dilution factor used is 5 to 10 times its initial volume. The concentrate diluted is concentrated again, by tangential filtration (Pellicon system) to a volume 2.5 to 3 times its initial volume. This concentrate is called C2.

The concentrate C2 is filtered in membrane with 0.2 μm of porosity, distributed in tubes/flasks and stored in a freezer at −80° C. (±5° C.). Samples are taken for quality control tests (Sterility and Bacterial Endotoxin, Mycoplasmas, Adventitious Agents in cells, Hemadsorbents Virus, Identity and Viral titration). After approbation in quality control tests, the Bulk is released to the formulation of monovalent vaccine.

The dengue virus Bulks lots produced in 2013 and 2014 are in table 1.

TABLE 1

Bulks of rDEN1Δ30-1545, rDEN2/4Δ30(ME)-1495,7163, rDEN3Δ30/31-7164, and rDEN4Δ30-7132,7163,8308 dengue virus produced in 2013 and 2014.

|  |  |  |  | Quality Control Tests |  |
|---|---|---|---|---|---|
| Bulks | Lots | Number of flasks | Viral titer $Log_{10}$PFU/ml | Bacterial Endotoxin (UE/mL) | Other tests |
| IB-DEN1Δ30/ Vero/M | 01/13 | 18 | 6.8 | <1.25 | Approved |
|  | 02/13 | 40 | 5.8 | <1.25 | Approved |
|  | 01/14 | 43 | 6.4 | <0.50 | Approved |
|  | 02/14 | 16 | 6.9 | <0.73 | Approved |
|  | 03/14 | 24 | 6.1 | <0.51 | Approved |
|  | 04/14 | 26 | 6.8 | <0.50 | Approved |
| IB-DEN2/ 4Δ30/Vero/M | 01/13 | 19 | 5.7 | <1.25 | Approved |
|  | 02/13 | 32 | 5.9 | <1.25 | Approved |
|  | 01/14 | 39 | 6.4 | <0.50 | Approved |
|  | 02/14 | 21 | 7.0 | 4.43 | Approved |
|  | 03/14 | 21 | 7.0 | <0.50 | Approved |
|  | 04/14 | 40 | 6.5 | <0.50 | Approved |
| IB-DEN3Δ30/ 31Vero/M | 01/13 | 17 | 6.1 | <1.25 | Approved |
|  | 02/13 | 45 | 6.1 | <1.25 | Approved |
|  | 02/14 | 22 | 6.8 | <0.50 | Approved |
|  | 03/14 | 23 | 6.6 | <0.50 | Approved |
| IB-DEN4Δ30/ Vero/M | 01/13 | 50 | 5.9 | <1.25 | Approved |
|  | 02/13 | 35 | 6.3 | <1.25 | Approved |
|  | 01/14 | 23 | 6.9 | 0.68 | Approved |
|  | 02/14 | 19 | 6.0 | <0.50 | Approved |
|  | 03/14 | 30 | 6.8 | 0.68 | Approved |

PS. The endotoxin value until 50 UE/mL is considered satisfactory, since the final product must be smaller or equal to 10 UE/mL.

STEP 7. Formulations of monovalent vaccines rDEN1Δ30-1545, rDEN2/4Δ30(ME)-1495,7163, rDEN3Δ30/31-7164, and rDEN4Δ30-7132,7163,8308 and dengue vaccine serotypes 1, 2, 3, 4 (attenuated)

Four dengue monovalent vaccines are formulated, one for each type of dengue virus (rDEN1Δ30-1545, rDEN2/4Δ30 (ME)-1495,7163, rDEN3Δ30/31-7164, and rDEN4Δ30-7132,7163,8308). The calculations for formulation consist in determining a dilution factor so that the monovalent vaccines according with each serotype are provided in the following amounts: 5.7±0.2, 5.6±0.2, 6.1±0.2 and 5.8±0.2 $Log_{10}$ PFU/ml for DENV1, DENV2, DENV3, and DENV4, respectively.

The formula to determine the dilution factor is: antilog of the bulk titer ($Log_{10}$ PFU/ml) divided by the antilog of viral titer ($Log_{10}$ PFU/ml) desired for each type of monovalent. The formulations of rDEN1Δ30-1545, rDEN2/4Δ30(ME)-1495,7163, rDEN3Δ30/31-7164, and rDEN4Δ30-7132, 7163,8308 monovalent are made with Leibovitz (L-15) medium without phenol red concentrate twice, i.e., the medium remains with its original components twice concentrated.

To make the dengue vaccine serotypes 1, 2, 3, 4 (attenuated) formulation, the monovalent 1, 2, 3 and 4 vaccines are mixed in the same ratio of volume. After homogenization of the formulated tetravalent vaccine, the product is subjected to a filtration (membrane with 0.2 μm of porosity) and samples are taken to the flowing quality control tests: Sterility, Bacterial Endotoxin, Viral Titration, pH, and Appearance of the product.

Step 8. Filling, Lyophilization and Sealing of the Tetravalent Dengue Vaccine.

After the tetravalent dengue vaccine formulation, the product is used to fill vials with 3 ml of vaccine. Samples of filled vials are taken for quality control tests (Sterility, Endotoxin Bacterial, Viral Titration, Appearance and pH).

After the filling of the vials they are transported to the lyophilizer and start the freeze-drying process. In this process, the following parameters are established: freezing (−30 to −50° C.), vacuum (20 to 100 μbar), drying from −30 to −50° C. (36 to 40 h), from −5 to −10° C. (18 to 24 h) and 25 to 29° C. (8 to 15 h).

At the end of freeze-drying process, the vials with the lyophilized vaccine are subjected to a sealing process. The final product, dengue vaccine 1, 2, 3, 4 (attenuated), is stored at 2-8° C. Samples of the vaccine lot are tested for Sterility, Bacterial Endotoxin, Viral Titration, Product Appearance before and after reconstitution with the diluent, pH, Residual DNA and Residual Moisture tests.

The product can be denominated dengue vaccine serotypes 1, 2, 3, 4 (attenuated), when following the Brazilian regulations for designation of vaccines.

The product can be reconstituted with 5.0 mL of the specific diluent to this vaccine (mixture of sodium phosphates), which corresponds to 10 doses/0.5 mL/vial. Each dose contains $10^{2.7}$ to $10^{3.7}$ PFU/dose of each of dengue virus used in the dengue vaccine 1, 2, 3, 4 (attenuated) formulation. The results of quality control tests obtained from six batches produced in 2014, are shown in table 2.

TABLE 2

Dengue vaccine serotypes 1, 2, 3, 4 (attenuated) lots produced in 2014.

| Lots | Viral titer $Log_{10}$/PFU/dose: DEN1 | DEN2 | DEN3 | DEN4 | Bacterial Endotoxin (UE/mL) | PH | Residual DNA (pg/dose) | Residual moisture % | Sterility Product appearance |
|---|---|---|---|---|---|---|---|---|---|
| 01/14 | 3.0 | 3.4 | 3.0 | 3.2 | <0.500 | 6.9 | 32.6 | 1.33 | Approved |
| 02/14 | 2.7 | 3.1 | 2.8 | 3.2 | <0.500 | 6.9 | 27.2 | 2.01 | Approved |
| 03/14 | 3.1 | 3.2 | 2.9 | 3.2 | <0.500 | 6.9 | 52.6 | 1.99 | Approved |
| 04/14 | 3.2 | 3.6 | 3.1 | 3.6 | 0.956 | 6.9 | 40.8 | 0.89 | Approved |
| 05/14 | 3.5 | 3.6 | 3.0 | 3.5 | 1.030 | 6.9 | 31.5 | 0.52 | Approved |
| 06/14 | 3.4 | 3.5 | 3.5 | 3.4 | <0.500 | 6.9 | 35.1 | 0.35 | Approved |

(Results of quality control tests)

Values for lot approval: Bacterial endotoxin=10 UE/ml; Viral titration=$10^{2.7}$ to $10^{3.7}$ PFU/dose; pH=6.8 to 7.2; Residual Cellular DNA≤100 pg/dose; Residual moisture≤3%; Product appearance before the reconstitution: slightly yellowish (homogeneous cake (SYHC) and Product appearance after reconstitution: slightly yellowish clear liquid (SYCL).

III Diluent for the Reconstitution of Dengue Vaccine 1, 2, 3, 4 (Attenuated)
Composition:
For the preparation of 1,000 mL

| | |
|---|---|
| Solution 1 (sodium phosphate monobasic dihydrate 0.2M) | 195 mL |
| Solution 2 (sodium phosphate dibasic heptahydrate, 0.2M) | 05 mL |
| WFI water qsp | 1,000 mL |

Presentation: vials or ampoules with 5.0 mL

IV Stability Studies of Dengue Vaccine 1, 2, 3, 4 (Attenuated) Stability Studies at 2-8° C.

The results of the tests carried out in the samples of three batches of dengue vaccine 1, 2, 3, 4 (attenuated) stored at 2-8° C. are shown in tables 3 and 4.

TABLE 3

Results of sterility and physical-chemical tests found in the lots of dengue vaccine 1, 2, 3, 4 (attenuated) stored at 2-8

| | | Results of Samples | | | |
|---|---|---|---|---|---|
| Vaccine Lots | Months of Storage 2-8° C. | Sterility | pH | Appearance before and after reconstitution | Residual moisture (%) |
| 01/10 | 12 | Approved | 7.1 | SYHC and SYCL | 2.91 |
| 02/10 | 12 | Approved | 7.1 | SYHC and SYCL | 2.79 |
| 01/11 | 12 | Approved | 7.1 | SYHC and SYCL | 2.48 |

SYHC: slightly yellowish homogeneous dried cake.
SYCL: slightly yellowish clear liquid.

III Diluent for the Reconstitution of Dengue Vaccine 1, 2, 3, 4 (Attenuated)
Composition:

The analysis of the results of Table 3 indicates that for up to at least one year of storage the titers of dengue virus serotypes 1, 2, 3 and 4 remained satisfactory. After 18 months of storage at 2-8° C., titers of DENV3 and DENV4 fell below the minimum required ($10^{2.7}$ PFU/dose of vaccine).

TABLE 4

Results of dengue virus titers components of dengue vaccine 1, 2, 3, 4 (attenuated) stored at 2-8° C.

| Vaccine | | Dengue virus titers ($Log_{10}$ PFU/dose) Months of Storage at 2-8° C. | | | | | |
|---|---|---|---|---|---|---|---|
| Lots | Serotypes | 0 | 3 | 6 | 9 | 12 | 18 |
| 01/10 | DEN1 | 3.1 | 3.2 | 3.3 | 3.3 | 3.1 | 3.0 |
| | DEN2 | 3.1 | 3.2 | 3.3 | 3.3 | 3.1 | 3.0 |
| | DEN3 | 3.2 | 3.3 | 3.1 | 3.1 | 3.2 | 2.0 |
| | DEN4 | 3.3 | 3.4 | 3.4 | 3.4 | 3.3 | 2.8 |
| 02/10 | DEN1 | 3.1 | 3.1 | 3.6 | 3.3 | 3.1 | 3.2 |
| | DEN2 | 3.2 | 3.2 | 3.3 | 3.3 | 3.2 | 3.0 |
| | DEN3 | 3.2 | 3.2 | 3.1 | 3.1 | 3.1 | 2.2 |
| | DEN4 | 3.2 | 3.2 | 3.4 | 3.4 | 3.2 | 2.2 |
| 01/11 | DEN1 | 3.1 | 3.4 | 3.1 | 3.1 | 3.1 | 3.0 |
| | DEN2 | 3.2 | 3.3 | 3.1 | 3.0 | 3.0 | 3.0 |
| | DEN3 | 3.2 | 3.1 | 3.1 | 3.1 | 3.0 | 2.4 |
| | DEN4 | 3.1 | 3.1 | 3.1 | 3.0 | 3.0 | 1.7 |

REFERENCES

[1] Bhatt S, Gething P W, Brady O J, Messina J P, Farlow A W, Moyes C L et. al 2013. The global distribution and burden of dengue. Nature; 496:504-507.
[2] Brady O J, Gething P W, Bhatt S, Messina J P, Brownstein J S, Hoen A G et al. Refining the global spatial limits of dengue virus transmission by evidence-based consensus. PLoS Negl Trop Dis. 2012; 6:e1760. doi:10.1371/journal.pntd.0001760.
[3] Ministério da Saúde Brazil. Boletim Epidemiológico. Monitoramento de casos de dengue. Vol. No 11.2015 in htt//portalsaude.gov.br/index.php/situação.e
[4] Ishikawa, T.; Yamanaka, A.; Konishi E. 2014. A review of successful flavivirus vaccines and the problems with those flaviviruses for which vaccines are not yet available. Vaccine. 32: 1326-1337.
[5] WHO (World Health Organization). Dengue vaccines. In the world wide web internet site "who.int/immunization/research/development/dengue_vaccines/en/"[accessed 30 Apr. 2015].
[6] Durbin A P, Karron R A, Sun W, Vaughn D W, Reynolds M J, Perreault J R, Thumar B, Men R, Lai C J, Elkins W R, Chanock R M, Murphy B R, Whitehead S S. Attenuation and immunogenicity in humans of a live dengue virus type-4 vaccine candidate with a 30 nucleotide deletion in its 3'-untranslated region. AM. J. Trop. Med. Hyg. (2001) November 65(5):405-13.
[7] Whitehead S S, Falgout B, Hanley K A, Blaney Jr J E Jr, Markoff L, Murphy B R. A live, attenuated dengue virus type 1 vaccine candidate with a 30-nucleotide deletion in the 3' untranslated region is highly attenuated and immunogenic in monkeys. J. Virol. (2003) January 77(2):1653-7.
[8] Wiggan O'Neil, Livengood J A, Silengo S J, Kinney R M, Osorio J E, Huang C Y H, Stinchcomb D T. Novel formulations enhance the thermal stability of live-attenuated flavivirus vaccines. Vaccine 29 (2011) 7456-7462.
[9] Burke C J, Hsu T-A, Volkin D B. Formulation, Stability and Delivery of Live Attenuated Vaccines for Human Use. Critical Review in Therapeutic Drug Carrier Systems (1999) 16(1):1-8.

Having described certain embodiments of the invention, one skilled in the art will appreciate in the appended claims that many modifications and variations of the present invention are possible in light of the above teachings. It is therefore, to be understood that, within the scope of the appended claims and disclosure provided herein, the invention may be practiced otherwise than as specifically described in certain embodiments.

The invention claimed is:

1. A process for preparing an attenuated tetravalent dengue vaccine comprising:
  (i) amplifying Vero cells in culture to produce Master and Working banks of Vero cells, wherein the Vero cells are adapted for growth in serum-free medium, are grown in serum-free medium, and are sub-cultured with trypsin of non-animal origin of this cell in 225 cm$^2$ Tissue Culture (TC)-flasks and later in a multi-layered cell culture system;
  (ii) infecting Vero cells from the Master or Working bank with dengue virus serotypes 1, 2, 3 and 4 from a Seed or Working bank of each virus, wherein the Vero cells are independently infected with dengue virus serotypes 1, 2, 3, and 4 in separate cultures with serum free medium;
  (iii) incubating the 225 cm$^2$ TC-flasks or multi-layered cell culture system containing the Vero cells infected with each dengue virus at 36.5° C. (±1° C.) for 10 to 20 days;
  (iv) harvesting the supernatants of each culture;
  (v) filtering each dengue virus suspension from step (iv) through a membrane with 0.2 μm of porosity and storing the filtered dengue virus at −80° C. (±5° C.);
  (vi) preparing dengue virus bulks of the serotypes 1, 2, 3 and 4;
  (vii) formulating monovalent vaccines;
  (viii) formulating tetravalent vaccine by mixing the monovalent vaccines;
  (ix) filling vials with the tetravalent vaccine;
  (x) lyophilizing the tetravalent vaccine in the vials;
  (xi) sealing the lyophilized tetravalent vaccine in the vials; and
  (xii) storing the lyophilized and sealed product at 2-8° C., thereby preparing an attenuated tetravalent dengue vaccine.

2. The process according to claim 1, wherein the supernatant is harvested in step (iv), an equal volume of serum free medium is added to the culture, and steps (iii) and (iv) are repeated.

3. The process according to claim 2, wherein steps (iii) and (iv) are repeated one to about seven times.

4. The process according to claim 1, wherein the dengue virus strains used are rDEN1Δ30-1545 (SEQ ID NO:1) or a variant thereof; rDEN2/4Δ30(ME)-1495,7163 (SEQ ID NO:2) or a variant thereof; rDEN3Δ30/31-7164 (SEQ ID NO:3) or a variant thereof, and rDEN4Δ30-7132,7163,8308 (SEQ ID NO:4) or a variant thereof.

5. A process for preparing an attenuated tetravalent dengue vaccine comprising:

(i) amplifying Vero cells in culture to produce Master and Working banks of Vero cells, wherein the Vero cells are adapted for growth in serum-free medium, are grown in serum-free medium, and are sub-cultured with trypsin of non-animal origin;

(ii) infecting Vero cells from the Master or Working bank with dengue virus serotypes 1, 2, 3 and 4 from a Seed or Working bank of each virus, wherein the Vero cells are independently infected with dengue virus serotypes 1, 2, 3, and 4 in separate cultures with serum free medium;

(iii) incubating the Vero cells infected with each dengue virus at 36.5° C. (±1° C.) for 10 to 20 days in a tissue culture flask or a multi-layered cell culture system;

(iv) harvesting the supernatants of each culture;

(v) filtering each dengue virus suspension from step (iv) through a membrane with 0.2 μm of porosity and storing the filtered dengue virus at −80° C. (±5° C.);

(vi) preparing dengue virus bulks of the serotypes 1, 2, 3 and 4;

(vii) formulating monovalent vaccines; and (viii) formulating tetravalent vaccine by mixing the monovalent vaccines.

6. The process according to claim 5 wherein the Vero cell line used is ATCC CCL-81.4.

7. The process according to claim 5, wherein the supernatant is harvested in step (iv), an equal volume of serum free medium is added to the culture, and steps (iii) and (iv) are repeated.

8. The process according to claim 7, wherein steps (iii) and (iv) are repeated one to about seven times.

9. The process according to claim 5, wherein the dengue virus strains used are rDEN1Δ30-1545 (SEQ ID NO:1) or a variant thereof; rDEN2/4Δ30(ME)-1495, 7163 (SEQ ID NO:2) or a variant thereof; rDEN3Δ30/31-7164 (SEQ ID NO:3) or a variant thereof and rDEN4Δ30-7132, 7163, 8308 (SEQ ID NO:4) or a variant thereof.

10. The process according to claim 9, wherein the multiplicity-of-infection (MOI) of dengue virus strains for each dengue serotype is: 0.01 to 0.03 for DENV 1 and 4, 0.02 to 0.04 for DENV 2, and 0.05 to 0.08 for DENV3.

11. The process according to claim 5, wherein the monovalent vaccines are mixed in the same ratio of volume to obtain the attenuated tetravalent dengue vaccine to serotypes 1, 2, 3, and 4.

12. The process according to claim 5, that further comprises the steps of filling vials with the tetravalent vaccine; lyophilizing the tetravalent vaccine in the vials; sealing the lyophilized tetravalent vaccine in the vials; and storing the lyophilized and sealed product at 2-8° C.

13. The process according to claim 12, wherein the parameters used in the lyophilizing process are: freezing (−30 to −50° C.), vacuum (20 to 100 μbar), primary drying from −30 to −50° C. (36 to 42 h) and −5 to −10° C. (18 to 24 h), and secondary drying from 25 to 29° C. (8 to 15 h).

14. A process for preparing a tetravalent dengue vaccine for administration to a subject that comprises the step of reconstituting a sealed and lyophilized tetravalent dengue vaccine produced by the process of claim 1 in a composition comprising 0.2M sodium phosphate monobasic dihydrate, 0.2M sodium phosphate dibasic heptahydrate, and water.

15. The process according to claim 14, wherein the sealed and lyophilized vaccine is reconstituted in 5 milliliters of the composition.

16. The process according to claim 1, wherein a stabilizer is added to the dengue virus bulks prior to formulating monovalent vaccines.

17. The process according to claim 16, wherein the stabilizer is galactose.

18. The process according to claim 5, wherein a stabilizer is added to the dengue virus bulks prior to formulating monovalent vaccines.

19. The process according to claim 18, wherein the stabilizer is galactose.

* * * * *

SEQUENCE LISTING

<160> NUMBER OF SEQ ID NOS: 4

<210> SEQ ID NO 1

-continued

<211> LENGTH: 10703
<212> TYPE: DNA
<213> ORGANISM: Dengue virus 1
<220> FEATURE:
<221> NAME/KEY: misc_feature
<222> LOCATION: (1)..(7)
<223> OTHER INFORMATION: n is a, c, g, or t

<400> SEQUENCE: 1

| | | | | | |
|---|---|---|---|---|---|
| nnnnnnnagt | ctacgtggac | cgacaagaac | agtttcgaat | cggaagcttg | cttaacgtag | 60 |
| ttctaacagt | tttttattag | agagcagatc | tctgatgaac | aaccaacgga | aaaagacggg | 120 |
| tcgaccgtct | ttcaatatgc | tgaaacgcgc | gagaaaccgc | gtgtcaactg | tttcacagtt | 180 |
| ggcgaagaga | ttctcaaaag | gattgctttc | aggccaagga | cccatgaaat | tggtgatggc | 240 |
| ttttatagca | ttcctaagat | ttctagccat | acctccaaca | gcaggaattt | tggctagatg | 300 |
| gggctcattc | aagaagaatg | gagcgatcaa | agtgttacgg | ggtttcaaga | agaaatctc | 360 |
| aaacatgttg | aacataatga | acaggaggaa | aagatctgtg | accatgctcc | tcatgctgct | 420 |
| gcccacagcc | ctggcgttcc | atctgaccac | ccgaggggga | gagccgcaca | tgatagttag | 480 |
| caagcaggaa | agaggaaaat | cacttttgtt | taagacctct | gcaggtgtca | acatgtgcac | 540 |
| ccttattgca | atggatttgg | gagagttatg | tgaggacaca | atgacctaca | aatgcccccg | 600 |
| gatcactgag | acggaaccag | atgacgttga | ctgttggtgc | aatgccacgg | agacatgggt | 660 |
| gacctatgga | acatgttctc | aaactggtga | acaccgacga | gacaaacgtt | ccgtcgcact | 720 |
| ggcaccacac | gtagggcttg | gtctagaaac | aagaaccgaa | acgtggatgt | cctctgaagg | 780 |
| cgcttggaaa | caaatacaaa | aagtggagac | ctgggctctg | agacacccag | gattcacggt | 840 |
| gatagccctt | tttctagcac | atgccatagg | aacatccatc | acccagaaag | ggatcatttt | 900 |
| tattttgctg | atgctggtaa | ctccatccat | ggccatgcgg | tgcgtgggaa | taggcaacag | 960 |
| agacttcgtg | gaaggactgt | caggagctac | gtgggtggat | gtggtactgg | agcatggaag | 1020 |
| ttgcgtcact | accatggcaa | aagacaaacc | aacactggac | attgaactct | tgaagacgga | 1080 |
| ggtcacaaac | cctgccgtcc | tgcgcaaact | gtgcattgaa | gctaaaatat | caaacaccac | 1140 |
| caccgattcg | agatgtccaa | cacaaggaga | agccacgctg | gtggaagaac | aggacacgaa | 1200 |
| ctttgtgtgt | cgacgaacgt | tcgtggacag | aggctggggc | aatggttgtg | ggctattcgg | 1260 |
| aaaaggtagc | ttaataacgt | gtgctaagtt | taagtgtgtg | acaaaactgg | aaggaaagat | 1320 |
| agtccaatat | gaaaacttaa | aatattcagt | gatagtcacc | gtacacactg | gagaccagca | 1380 |
| ccaagttgga | aatgagacca | cagaacatgg | aacaactgca | accataacac | ctcaagctcc | 1440 |
| cacgtcggaa | atacagctga | cagactacgg | agctctaaca | ttggattgtt | cacctagaac | 1500 |
| agggctagac | tttaatgaga | tggtgttgtt | gacaatggaa | aaacgatcgt | ggctcgtcca | 1560 |
| caaacaatgg | tttctagact | taccactgcc | ttggacctcg | ggggcttcaa | catcccaaga | 1620 |
| gacttggaat | agacaagact | tgctggtcac | atttaagaca | gctcatgcaa | aaaagcagga | 1680 |
| agtagtcgta | ctaggatcac | aagaaggagc | aatgcacact | gcgttgactg | gagcgacaga | 1740 |
| aatccaaacg | tctggaacga | caacaatttt | tgcaggacac | ctgaaatgca | gactaaaaat | 1800 |
| ggataaactg | actttaaaag | ggatgtcata | tgtaatgtgc | acagggtcat | tcaagttaga | 1860 |
| gaaggaagtg | gctgagaccc | agcatggaac | tgttctagtg | caggttaaat | acgaaggaac | 1920 |
| agatgcacca | tgcaagatcc | ccttctcgtc | ccaagatgag | aagggagtaa | cccagaatgg | 1980 |
| gagattgata | acagccaacc | ccatagtcac | tgacaaagaa | aaaccagtca | acattgaagc | 2040 |
| ggagccacct | tttggtgaga | gctacattgt | ggtaggagca | ggtgaaaaag | ctttgaaact | 2100 |

```
aagctggttc aagaagggaa gcagtatagg gaaaatgttt gaagcaactg cccgtggagc   2160
acgaaggatg gccatcctgg gagacactgc atgggacttc ggttctatag gaggggtgtt   2220
cacgtctgtg ggaaaactga tacaccagat ttttgggact gcgtatggag ttttgttcag   2280
cggtgtttct tggaccatga agataggaat agggattctg ctgacatggc taggattaaa   2340
ctcaaggagc acgtcccttt caatgacgtg tatcgcagtt ggcatggtca cactgtacct   2400
aggagtcatg gttcaggcgg actcgggatg tgtaatcaac tggaaaggca gagaactcaa   2460
atgtggaagc ggcatttttg tcaccaatga agtccacacc tggacagagc aatataaatt   2520
ccaggccgac tcccctaaga gactatcagc ggccattggg aaggcatggg aggagggtgt   2580
gtgtggaatt cgatcagcca ctcgtctcga gaacatcatg tggaagcaaa tatcaaatga   2640
attaaaccac atcttacttg aaaatgacat gaaatttaca gtggtcgtag agacgttag    2700 tggaatcttg gcccaaggaa agaaaatgat taggccacaa cccatggaac acaaatactc   2760
gtggaaaagc tggggaaaag ccaaaatcat aggagcagat gtacagaata ccaccttcat   2820
catcgacggc ccaaacaccc cagaatgccc tgataaccaa agagcatgga acatttggga   2880
agttgaagac tatggatttg gaattttcac gacaaacata tggttgaaat tgcgtgactc   2940
ctacactcaa gtgtgtgacc accggctaat gtcagctgcc atcaaggata gcaaagcagt   3000
ccatgctgac atggggtact ggatagaaag tgaaaagaac gagacttgga agttggcaag   3060
agcctccttc atagaagtta agacatgcat ctggccaaaa tcccacactc tatggagcaa   3120
tggagtcctg gaaagtgaga tgataatccc aaagatatat ggaggaccaa tatctcagca   3180
caactacaga ccaggatatt tcacacaaac agcagggccg tggcacttgg gcaagttaga   3240
actagatttt gatttatgtg aaggtaccac tgttgttgtg gatgaacatt gtggaaatcg   3300
aggaccatct cttagaacca caacagtcac aggaaagaca atccatgaat ggtgctgtag   3360
atcttgcacg ttaccccccc tacgtttcaa aggagaagac gggtgctggt acggcatgga   3420
aatcagacca gtcaaggaga aggaagagaa cctagttaag tcaatggtct ctgcagggtc   3480
aggagaagtg gacagttttt cactaggact gctatgcata tcaataatga tcgaagaggt   3540
aatgagatcc agatggagca gaaaaatgct gatgactgga acattggctg tgttcctcct   3600
tctcacaatg ggacaattga catggaatga tctgatcagg ctatgtatca tggttggagc   3660
caacgcttca gacaagatgg ggatgggaac aacgtaccta gctttgatgg ccactttcag   3720
aatgagacca atgttcgcag tcgggctact gtttcgcaga ttaacatcta gagaagttct   3780
tcttcttaca gttggattga gtctggtggc atctgtagaa ctaccaaatt ccttagagga   3840
gctaggggat ggacttgcaa tgggcatcat gatgttgaaa ttactgactg attttcagtc   3900
acatcagcta tgggctacct tgctgtcttt aacatttgtc aaaacaactt tttcattgca   3960
ctatgcatgg aagacaatgg ctatgatact gtcaattgta tctctcttcc ctttatgcct   4020
gtccacgact tctcaaaaaa caacatggct tccggtgttg ctgggatctc ttggatgcaa   4080
accactaacc atgtttctta aacagaaaaa caaaatctgg ggaaggaaaa gctggcctct   4140
caatgaagga attatggctg ttggaatagt tagcattctt ctaagttcac ttctcaagaa   4200
tgatgtgcca ctagctggcc cactaatagc tggaggcatg ctaatagcat gttatgtcat   4260
atctggaagc tcggccgatt tatcactgga gaaagcggct gaggtctcct gggaagaaga   4320
agcagaaaca tctggtgcct cacacaacat actagtggag gtccaagatg atggaaccat   4380
gaaaataaag gatgaagaga gagatgacac actcaccatt ctcctcaaag caactctgct   4440
```

```
agcaatctca ggggtatacc caatgtcaat accggcgacc ctctttgtgt ggtattttg     4500 gcagaaaaag aaacagagat caggagtgct atgggacaca cccagccctc cagaagtgga    4560
aagagcagtc cttgatgatg gcatttatag aattctccaa agaggattgt tgggcaggtc    4620
tcaagtggga gtaggagttt ttcaagaagg cgtgttccac acaatgtggc acgtcaccag    4680
gggagctgtc ctcatgtacc aagggaagag actggaacca agttgggcca gtgtcaaaaa    4740
agacttgatc tcatatggag gaggttggag gtttcaagga tcctggaacg cgggagaaga    4800
agtgcaggtg attgctgttg aaccggggaa gaaccccaaa aatgtacaga cagcgccggg    4860
taccttcaag accectgaag gcgaagttgg agccatagct ctagacttta aacccggcac    4920
atctggatct cctatcgtga acagagaggg aaaaatagta ggtctttatg gaaatggagt    4980
ggtgacaaca agtggtacct acgtcagtgc catagctcaa gctaaagcat cacaagaagg    5040
gcctctacca gagattgagg acgaggtgtt taggaaaaga aacttaacaa taatggacct    5100
acatccagga tcgggaaaaa caagaagata ccttccagcc atagtccgtg aggccataaa    5160
aagaaagctg cgcacgctag tcttagctcc cacaagagtt gtcgcttctg aaatggcaga    5220
ggcgctcaag ggaatgccaa taaggtatca gacaacagca gtgaagagtg aacacacggg    5280
aaaggagata gttgacctta tgtgtcacgc cactttcact atgcgtctcc tgtctcctgt    5340
gagagttccc aattataata tgattatcat ggatgaagca catttcaccg atccagccag    5400
catagcagcc agagggtata tctcaacccg agtgggtatg ggtgaagcag ctgcgatttt    5460
catgacagcc actccccccg gatcggtgga ggcctttcca cagagcaatg cagttatcca    5520
agatgaggaa agagacattc ctgaaagatc atggaactca ggctatgact ggatcactga    5580
tttcccaggt aaaacagtct ggtttgttcc aagcatcaaa tcaggaaatg acattgccaa    5640
ctgtttaaga aagaatggga aacgggtggt ccaattgagc agaaaaactt ttgacactga    5700
gtaccagaaa acaaaaaata cgactggga ctatgttgtc acaacagaca tatccgaaat    5760
gggagcaaac ttccgagccg acaggggtaat agacccgagg cggtgcctga aaccggtaat    5820
actaaaagat ggcccagagc gtgtcattct agccggaccg atgccagtga ctgtggctag    5880
cgccgcccag aggagaggaa gaattggaag gaaccaaaat aaggaaggcg atcagtatat    5940
ttacatggga cagcctctaa aaatgatga ggaccacgcc cattggacag aagcaaaaat    6000
gctccttgac aacataaaca caccagaagg gattatccca gccctctttg agccggagag    6060
agaaaagagt gcagcaatag acgggaata cagactacgg ggtgaagcga ggaaaacgtt    6120
cgtggagctc atgagaagag gagatctacc tgtctggcta tcctacaaag ttgcctcaga    6180
aggcttccag tactccgaca aaggtggtg ctttgatggg gaaaggaaca accaggtgtt    6240
ggaggagaac atggacgtgg agatctggac aaaagaagga gaaagaaaga aactacgacc    6300
ccgctggctg gatgccagaa catactctga cccactggct ctgcgcgaat tcaaagagtt    6360
cgcagcagga agaagaagcg tctcaggtga cctaatatta gaaataggga aacttccaca    6420
acatttaacg caaagggccc agaacgcctt ggacaatctg gttatgttgc acaactctga    6480
acaaggagga aaagcctata gacacgccat ggaagaacta ccagacacca tagaaacgtt    6540
aatgctccta gctttgatag ctgtgctgac tggtggagtg acgttgttct tcctatcagg    6600
aaggggtcta ggaaaaacat ccattggcct actctgcgtg attgcctcaa gtgcactgtt    6660
atggatggcc agtgtggaac cccattggat agcggcctct atcatactgg agttcttct    6720 gatggtgttg cttattccag agccggacag acagcgcact ccacaagaca accagctagc    6780
atacgtggtg ataggtctgt tattcatgat attgacagtg gcagccaatg agatgggatt    6840
```

```
actggaaacc acaaagaagg acctggggat tggtcatgca gctgctgaaa accaccatca   6900
tgctgcaatg ctggacgtag acctacatcc agcttcagcc tggactctct acgcagtggc   6960
cacaacaatt atcactccca tgatgagaca cacaattgaa aacacaacgg caaatatttc   7020
cctgacagct attgcaaacc aggcagctat attgatggga cttgacaagg gatggccaat   7080
atcaaagatg gacataggag ttccacttct cgccttgggg tgctattctc aggtgaaccc   7140
gctgacgctg acagcggcgg tatttatgct agtggctcat tatgccataa ttggacccgg   7200
actgcaagca aaagctacta gagaagctca aaaaggaca gcagccggaa taatgaaaaa   7260
cccaactgtc gacgggatcg ttgcaataga tttggaccct gtggtttacg atgcaaaatt   7320
tgaaaaacag ctaggccaaa taatgttgtt gatactttgc acatcacaga tcctcctgat   7380
gcggaccaca tgggccttgt gtgaatccat cacactagcc actggacctc tgaccacgct   7440
ttgggaggga tctccaggaa aattctggaa caccacgata gcggtgtcca tgcaaacat   7500
ttttagggga agttatctag caggagcagg tctggccttt tcattaatga aatctctagg   7560
aggaggtagg agaggcacgg gagcccaagg ggaaacactg ggagaaaaat ggaaaagaca   7620
gctaaaccaa ttgagcaagt cagaattcaa cacttacaaa aggagtggga ttatagaggt   7680
ggatagatct gaagccaaag aggggttaaa aagaggagaa acgactaaac acgcagtgtc   7740
gagaggaacg gccaaactga ggtggttttgt ggagaggaac cttgtgaaac cagaagggaa   7800
agtcatagac ctcggttgtg gaagaggtgg ctggtcatat tattgcgctg ggctgaagaa   7860
agtcacagaa gtgaaaggat acacgaaagg aggacctgga catgaggaac caatcccaat   7920
ggcaacctat ggatggaacc tagtaaagct atactccggg aaagatgtat tctttacacc   7980
acctgagaaa tgtgacaccc tcttgtgtga tattggtgag tcctctccga acccaactat   8040
agaagaagga agaacgttac gtgttctaaa gatggtggaa ccatggctca gaggaaacca   8100
attttgcata aaaattctaa atccctatat gccgagtgtg gtagaaactt tggagcaaat   8160
gcaaagaaaa catggaggaa tgctagtgcg aaatccactc tcaagaaact ccactcatga   8220
aatgtactgg gtttcatgtg aacaggaaa cattgtgtca gcagtaaaca tgacatctag   8280
aatgctgcta aatcgattca caatggctca caggaagcca acatatgaaa gagacgtgga   8340
cttaggcgct ggaacaagac atgtggcagt agaaccagag gtggccaacc tagatatcat   8400
tggccagagg atagagaata taaaaaatga acacaaatca acatggcatt atgatgagga   8460
caatccatac aaaacatggg cctatcatgg atcatatgag gtcaagccat caggatcagc   8520
ctcatccatg gtcaatggtg tggtgagact gctaaccaaa ccatgggatg tcattcccat   8580
ggtcacacaa atagccatga ctgacaccac accctttgga caacagaggg tgttaaaga   8640
gaaagttgac acgcgtacac caaaagcgaa acgaggcaca gcacaaatta tggaggtgac   8700
agccaggtgg ttatgggggtt ttctctctag aaacaaaaaa cccagaatct gcacaagaga   8760
ggagttcaca agaaaagtca ggtcaaacgc agctattgga gcagtgttcg ttgatgaaaa   8820
tcaatggaac tcagcaaaag aggcagtgga agatgaacgg ttctgggacc ttgtgcacag   8880
agagagggag cttcataaac aaggaaaatg tgccacgtgt gtctacaaca tgatgggaaa   8940
gagagagaaa aaattaggag agttcggaaa ggcaaaagga agtcgcgcaa tatggtacat   9000
gtggttggga gcgcgctttt tagagtttga agcccttggt ttcatgaatg aagatcactg   9060
gttcagcaga gagaattcac tcagtggagt ggaaggagaa ggactccaca acttggata   9120
catactcaga gacatatcaa agattccagg gggaaatatg tatgcagatg acacagccgg   9180
```

-continued

```
atgggacaca agaataacag aggatgatct tcagaatgag gccaaaatca ctgacatcat   9240
ggaacctgaa catgccctat tggccacgtc aatctttaag ctaacctacc aaaacaaggt   9300
agtaagggtg cagagaccag cgaaaaatgg aaccgtgatg gatgtcatat ccagacgtga   9360
ccagagagga agtggacagg ttggaaccta tggcttaaac accttcacca acatggaggc   9420
ccaactaata agacaaatgg agtctgaggg aatcttttca cccagcgaat tggaaacccc   9480
aaatctagcc gaaagagtcc tcgactggtt gaaaaaacat ggcaccgaga ggctgaaaag   9540
aatggcaatc agtggagatg actgtgtggt gaaaccaatt gatgacagat ttgcaacagc   9600
cttaacagct ttgaatgaca tgggaaaggt aagaaaagac ataccgcaat gggaaccttc   9660
aaaaggatgg aatgattggc aacaagtgcc tttctgttca caccatttcc accagctgat   9720
tatgaaggat gggagggaga tagtggtgcc atgccgcaac caagatgaac ttgtaggtag   9780
ggccagagta tcacaaggcg ccggatggag cttgagagaa actgcatgcc taggcaagtc   9840
atatgcacaa atgtggcagc tgatgtactt ccacaggaga gacttgagat tagcggctaa   9900
tgctatctgt tcagccgttc cagttgattg ggtcccaacc agccgtacca cctggtcgat   9960
ccatgcccac catcaatgga tgacaacaga agacatgttg tcagtgtgga atagggtttg  10020
gatagaggaa aacccatgga tggaggacaa gactcatgtg tccagttggg aagacgttcc  10080
atacctagga aaaagggaag atcaatggtg tggatcccta ataggcttaa cagcacgagc  10140
cacctgggcc accaacatac aagtggccat aaaccaagtg agaaggctca ttgggaatga  10200
gaattatcta gacttcatga catcaatgaa gagattcaaa aacgagagtg atcccgaagg  10260
ggcactctgg taagccaact cattcacaaa ataaaggaaa ataaaaaatc aaacaaggca  10320
agaagtcagg ccggattaag ccatagcacg gtaagagcta tgctgcctgt gagccccgtc  10380
caaggacgta aaatgaagtc aggccgaaag ccacggttcg agcaagccgt gctgcctgta  10440
gctccatcgt ggggatgtaa aaacccggga ggctgcaaac catggaagct gtacgcatgg  10500
ggtagcagac tagtggttag aggagacccc tcccaagaca caacgcagca gcggggccca  10560
agactagagg ttagaggaga cccccccgcac aacaacaaac agcatattga cgctgggaga  10620
gaccagagat cctgctgtct ctacagcatc attccaggca cagaacgcca gaaaatggaa  10680
tggtgctgtt gaatcaacag gtt                                           10703
```

```
<210> SEQ ID NO 2
<211> LENGTH: 10618
<212> TYPE: DNA
<213> ORGANISM: Dengue virus 2
<220> FEATURE:
<221> NAME/KEY: misc_feature
<222> LOCATION: (1)..(23)
<223> OTHER INFORMATION: n is a, c, g, or t
<220> FEATURE:
<221> NAME/KEY: misc_feature
<222> LOCATION: (10580)..(10618)
<223> OTHER INFORMATION: n is a, c, g, or t

<400> SEQUENCE: 2
```

```
nnnnnnnnnn nnnnnnnnnn nnncaaggac agttccaaat cggaagcttg cttaacacag     60
ttctaacagt ttgtttgaat agagagcaga tctctggaaa aatgaaccaa cgaaaaaagg    120
tggttagacc acctttcaat atgctgaaac gcgagagaaa ccgcgtatca acccctcaag    180
ggctggtgaa gagattctca accggacttt tttctgggaa aggaccctta cggatggtgc    240
tagcattcat cacgtttttg cgagtccttt ccatcccacc aacagcaggg attctgaaga    300
gatggggaca gttgaagaaa aataaggcca tcaagatact gattggattc aggaaggaga    360
```

```
taggccgcat gctgaacatc ttgaacggga gaaaaaggtc tgcaggcatg atcattatgc      420
tgattccaac agtgatggcg ttccatttaa ccacacgtaa cggagaacca cacatgatcg      480
tcagtagaca agagaaaggg aaaagtcttc tgtttaaaac agaggatggt gtgaacatgt      540
gtaccctcat ggccatggac cttggtgaat tgtgtgaaga tacaatcacg tacaagtgtc      600
ctcttctcag gcagaatgaa ccagaagaca tagattgttg gtgcaactct acgtccacat      660
gggtaactta tgggacgtgt accaccacag gagaacacag aagagaaaaa agatcagtgg      720
cactcgttcc acatgtggga atgggactgg agacacgaac tgaaacatgg atgtcatcag      780
aaggggcctg gaaacatgcc cagagaattg aaacttggat cttgagacat ccaggcttta      840
ccataatggc agcaatcctg gcatacacca taggaacgac acatttccaa agagccctga      900 tttctcatctt actgacagct gtcgctcctt caatgacaat gcgttgcata ggaatatcaa      960
atagagactt tgtagaaggg gtttcaggag gaagctgggt tgacatagtc ttagaacatg     1020
gaagctgtgt gacgacgatg gcaaaaaaca aaccaacatt ggattttgaa ctgataaaaa     1080
cagaagccaa acaacctgcc actctaagga agtactgtat agaggcaaag ctgaccaaca     1140
caacaacaga atctcgctgc ccaacacaag gagaacctag cctaaatgaa gagcaggaca     1200
aaaggttcgt ctgcaaacac tccatggtgg acagaggatg gggaaatgga tgtggattat     1260
ttggaaaagg aggcattgtg acctgtgcta tgttcacatg caaaaagaac atggaaggaa     1320
aagtcgtgca accagaaaac ttggaataca ccattgtgat aacacctcac tcaggggaag     1380
agcatgcagt cggaaatgac acaggaaaac atggcaagga atcaaaata acaccacaga     1440 gttccatcac agaagcagag ttgacaggct atggcactgt cacgatggaa tgctttccga     1500
gaacgggcct cgacttcaat gagatggtgt tgctgcaaat ggaaaataaa gcttggctgg     1560
tgcacaggca atggttccta gacctgccgt tgccatggct gcccggagcg acacacaag     1620 gatcaaattg gatacagaaa gagacattgg tcactttcaa aaatccccat gcgaagaaac     1680
aggatgttgt tgtttttggga tcccaagaag gggccatgca cacagcactc acaggggcca     1740
cagaaatcca gatgtcatca ggaaacttac tgttcacagg acatctcaag tgcaggctga     1800
ggatggacaa actacagctc aaaggaatgt catactctat gtgcacagga aagtttaaag     1860
ttgtgaagga aatagcagaa acacaacatg gaacaatagt tatcagagta caatatgaag     1920
gggacggttc tccatgtaag atcccttttg agataatgga tttggaaaaa agacatgttt     1980
taggtcgcct gattacagtc aacccaatcg taacagaaaa agatagccca gtcaacatag     2040
aagcagaacc tccattcgga gacagctaca tcatcatagg agtagagccg ggacaattga     2100
agctcaactg gtttaagaaa ggaagttcta tcggccaaat gtttgagaca acaatgaggg     2160
gagcgaagag aatggccatt ttaggtgaca gcttggga ttttggatcc ctgggaggag     2220
tgtttacatc tataggaaag gctctccacc aagttttcgg agcaatctat ggggctgcct     2280
tcagtggggt ctcatggact atgaaaatcc tcataggagt cattatcaca tggataggaa     2340
tgaactcgag gaacacttca atggctatga cgtgcatagc tgttggagga atcactctgt     2400
ttctgggctt cacagttcaa gcagacatgg gttgtgtggc gtcatggagt gggaaagaat     2460
tgaagtgtgg aagcggaatt tttgtggttg acaacgtgca cacttggaca gaacagtaca     2520
aatttcaacc agagtcccca gcgagactag cgtctgcaat attaaatgcc cacaaagatg     2580
gggtctgtgg aattagatca accacgaggc tggaaaatgt catgtggaag caaataacca     2640
acgagctaaa ctatgttctc tgggaaggag acatgaccct cactgtagtg gctggggatg     2700
```

```
tgaaggggt gttgaccaaa ggcaagagag cactcacacc cccagtgagt gatctgaaat    2760
attcatggaa gacatgggga aaagcaaaaa tcttcacccc agaagcaaga aatagcacat    2820
ttttaataga cggaccagac acctctgaat gccccaatga acgaagagca tggaactctc    2880
ttgaggtgga agactatgga tttggcatgt tcacgaccaa catatggatg aaattccgag    2940
aaggaagttc agaagtgtgt gaccacaggt taatgtcagc tgcaattaaa gatcagaaag    3000
ctgtgcatgc tgacatgggt tattggatag agagctcaaa aaaccagacc tggcagatag    3060
agaaagcatc tcttattgaa gtgaaaacat gtctgtggcc caagacccac acactgtgga    3120
gcaatggagt gctggaaagc cagatgctca ttccaaaatc atatgcgggc ccttttttcac    3180 agcacaatta ccgccagggc tatgccacgc aaaccgtggg cccatggcac ttaggcaaat    3240
tagagataga ctttggagaa tgccccggaa caacagtcac aattcaggag gattgtgacc    3300
atagaggccc atctttgagg accaccactg catctggaaa actagtcacg caatggtgct    3360
gccgctcctg cacgatgcct cccttaaggt tcttgggaga agatgggtgc tggtatggga    3420
tggagattag gcccttgagt gaaaagaag agaacatggt caaatcacag gtgacggccg    3480
gacagggcac atcagaaact ttttctatgg gtctgttgtg cctgaccttg tttgtggaag    3540
aatgcttgag gagaagagtc actaggaaac acatgatatt agttgtggtg atcactcttt    3600
gtgctatcat cctgggaggc ctcacatgga tggacttact acgagccctc atcatgttgg    3660
gggacaccat gtctggtaga ataggaggac agatccacct agccatcatg gcagtgttca    3720
agatgtcacc aggatacgtg ctgggtgtgt ttttaaggaa actcacttca agagagacag    3780
cactaatggt aataggaatg gccatgacaa cggtgctttc aattccacat gaccttatgg    3840
aactcattga tggaatatca ctgggactaa ttttgctaaa aatagtaaca cagtttgaca    3900
acacccaagt gggaacctta gctctttcct tgactttcat aagatcaaca atgccattgg    3960
tcatggcttg gaggaccatt atggctgtgt tgtttgtggt cacactcatt cctttgtgca    4020
ggacaagctg tcttcaaaaa cagtctcatt gggtagaaat aacagcactc atcctaggag    4080
cccaagctct gccagtgtac ctaatgactc ttatgaaagg agcctcaaga agatcttggc    4140
ctcttaacga gggcataatg gctgtgggtt tggttagtct cttaggaagc gctctttaa    4200 agaatgatgt cccctttagct ggcccaatgg tggcaggagg cttacttctg gcggcttacg    4260
tgatgagtgg tagctcagca gatctgtcac tagagaaggc cgccaacgtg cagtgggatg    4320
aaatggcaga cataacaggc tcaagcccaa tcatagaagt gaagcaggat gaagatggct    4380 cttttctccat acgggacgtc gaggaaacca atatgataac ccttttggtg aaactggcac    4440
tgataacagt gtcaggtctc taccccttgg caattccagt cacaatgacc ttatggtaca    4500
tgtggcaagt gaaaacacaa agatcaggag ccctgtggga cgtcccctca cccgctgcca    4560
ctaaaaaagc cgcactgtct gaaggagtgt acaggatcat gcaaagaggg ttattcggga    4620
aaactcaggt tggagtaggg atacacatgg aaggtgtatt tcacacaatg tggcatgtaa    4680
caagaggatc agtgatctgc cacgagactg ggagattgga gccatcttgg gctgacgtca    4740
ggaatgacat gatatcatac ggtgggggat ggaggcttgg agacaaatgg gacaaagaag    4800
aagacgttca ggtcctcgcc atagaaccag gaaaaaatcc taaacatgtc caaacgaaac    4860
ctggcctttt caagacccta actggagaaa ttggagcagt aacattagat ttcaaacccg    4920
gaacgtctgg ttctcccatc atcaacagga aggaaagt catcggactc tatggaaatg    4980
gagtagttac caaatcaggt gattacgtca gtgccataac gcaagccgaa agaattggag    5040
agccagatta tgaagtggat gaggacattt ttcgaaagaa aagattaact ataatggact    5100
```

```
tacaccccgg agctggaaag acaaaaagaa ttcttccatc aatagtgaga gaagccttaa    5160
aaaggaggct acgaactttg attttagctc ccacgagagt ggtggcggcc gagatggaag    5220
aggccctacg tggactgcca atccgttatc agaccccagc tgtgaaatca aacacacag     5280 gaagagagat tgtagacctc atgtgtcatg caaccttcac aacaagactt ttgtcatcaa    5340
ccagggttcc aaattacaac cttatagtga tggatgaagc acatttcacc gatccttcta    5400
gtgtcgcggc tagaggatac atctcgacca gggtggaaat gggagaggca gcagccatct    5460
tcatgaccgc aaccctccc ggagcgacag atccctttcc ccagagcaac agcccaatag     5520
aagacatcga gagggaaatt ccggaaaggt catggaacac agggttcgac tggataacag    5580
actaccaagg gaaaactgtg tggtttgttc ccagcataaa agctggaaat gacattgcaa    5640
attgtttgag aaagtcggga aagaaagtta tccagttgag taggaaaacc tttgatacag    5700
agtatccaaa aacgaaactc acggactggg actttgtggt cactacagac atatctgaaa    5760
tgggggccaa ttttagagcc gggagagtga tagaccctag aagatgcctc aagccagtta    5820
tcctaccaga tgggccagag agagtcattt tagcaggtcc tattccagtg actccagcaa    5880
gcgctgctca gagaagaggg cgaataggaa ggaacccagc acaagaagac gaccaatacg    5940
ttttctccgg agacccacta aaaaatgatg aagatcatgc ccactggaca gaagcaaaga    6000
tgctgcttga caatatctac accccagaag ggatcattcc aacattgttt ggtccggaaa    6060
gggaaaaaac ccaagccatt gatggagagt ttcgcctcag aggggaacaa aggaagactt    6120
ttgtggaatt aatgaggaga ggagaccttc cggtgtggct gagctataag gtagcttctg    6180
ctggcatttc ttacaaagat cgggaatggt gcttcacagg ggaaagaaat aaccaaattt    6240
tagaagaaaa catggaggtt gaaatttgga ctagagaggg agaaaagaaa agctaaggc     6300 caagatggtt agatgcacgt gtatacgctg accccatggc tttgaaggat ttcaaggagt    6360
ttgccagtgg aaggaagagt ataactctcg acatcctaac agagattgcc agtttgccaa    6420 cttaccttc ctctagggcc aagctcgccc ttgataacat agtcatgctc cacacaacag     6480
aaagaggagg gagggcctat caacacgccc tgaacgaact tccggagtca ctggaaacac    6540
tcatgcttgt agctttacta ggtgctatga cagcaggcat cttcctgttt ttcatgcaag    6600
ggaaaggaat agggaaattg tcaatggggtt tgataaccat tgcggtggct agtggcttgc    6660
tctgggtagc agaaattcaa ccccagtgga tagcggcctc aatcatacta gagttttttc    6720
tcatggtact gttgataccg gaaccagaaa aacaaaggac cccacaagac aatcaattga    6780
tctacgtcat attgaccatt ctcaccatca ttggtctaat agcagccaac gagatggggc    6840
tgattgaaaa aacaaaaacg gattttgggt tttaccagt aaaaacagaa accaccatcc      6900
tcgatgtgga cttgagacca gcttcagcat ggacgctcta tgcagtagcc accacaattc    6960
tgactcccat gctgagacac accatagaaa acacgtcggc caacctatct ctagcagcca    7020
ttgccaacca ggcagccgtc ctaatggggc ttggaaaagg atggccgctc cacagaatgg    7080
acctcggtgt gccgctgtta gcaatgggat gctattctca agtgaaccca acaaccttga    7140
cagcatcctt agtcatgctt ttcgtgcact atgcaataat aggcccagga ttgcaggcaa    7200
aagccacaag agaggcccag aaaaggacag ctgctgggat catgaaaaat cccacagtgg    7260
acgggataac agtaatagat ctagaaccaa tatcctatga cccaaaattt gaaaagcaat    7320
tagggcaggt catgctacta gtcttgtgtg ctggacaact actcttgatg agaacaacat    7380
gggcttctct tgaagtcttg actttggcca caggaccaat cttgaccttg tgggagggca    7440
```

```
acccgggaag gttttggaac acgaccatag ccgtatccac cgccaacatt ttcagggaa    7500
gttacttggc gggagctgga ctggcttttt cactcataaa gaatgcacaa acccctagga   7560
ggggaactgg gaccacagga gagacactgg gagagaagtg gaagagacag ctaaactcat   7620
tagacagaaa agagtttgaa gagtataaaa gaagtggaat actagaagtg gacaggactg   7680
aagccaagtc tgccctgaaa gatgggtcta aaatcaagca tgcagtatca agagggtcca   7740
gtaagatcag atggattgtt gagagaggga tggtaaagcc aaaagggaaa gttgtagatc   7800
ttggctgtgg gagaggagga tggtcttatt acatggcgac actcaagaac gtgactgaag   7860
tgaaagggta tacaaaagga ggtccaggac atgaagaacc gattcccatg gctacttatg   7920
gttggaattt ggtcaaactc cattcagggg ttgacgtgtt ctacaaaccc acagagcaag   7980
tggacaccct gctctgtgat attggggagt catcttctaa tccaacaata gaggaaggaa   8040
gaacattaag agttttgaag atggtggagc catggctctc ttcaaaacct gaattctgca   8100
tcaaagtcct taaccccctac atgccaacag tcatagaaga gctggagaaa ctgcagagaa   8160
aacatggtgg gaaccttgtc agatgcccgc tgtccaggaa ctccacccat gagatgtatt   8220
gggtgtcagg agcgtcggga acattgtga gctctgtgaa cacaacatca agatgttgt    8280
tgaacaggtt cacaacaagg cataggaaac ccacttatga gaaggacgta gatcttgggg   8340
caggaacgag aagtgtctcc actgaaacag aaaaaccaga catgacaatc attgggagaa   8400
ggcttcagcg attgcaagaa gagcacaaag aaacctggca ttatgatcag gaaaacccat   8460
acagaacctg ggcgtatcat ggaagctatg aagctccttc gacaggctct gcatcctcca   8520
tggtgaacgg ggtggtaaaa ctgctaacaa accctgggaa tgtgattcca atggtgactc   8580
agttagccat gacagataca accccttttg ggcaacaaag agtgttcaaa gagaaggtgg   8640
ataccagaac accacaacca aaacccggta cacgaatggt tatgaccacg acagccaatt   8700
ggctgtgggc cctccttgga aagaagaaaa atcccagact gtgcacaagg gaagagttca   8760
tctcaaaagt tagatcaaac gcagccatag gcgcagtctt tcaggaagaa cagggatgga   8820
catcagccag tgaagctgtg aatgacagcc ggttttggga actggttgac aaagaagggg   8880
ccctacacca ggaagggaaa tgtgaatcgt gtgtctataa catgatggga aaacgtgaga   8940
aaaagttagg agagtttggc agagccaagg gaagccgagc aatctggtac atgtggctgg   9000
gagcgcggtt tctggaattt gaagccctgg gtttttgaa tgaagatcac tggtttggca   9060
gagaaaattc atggagtgga gtggaagggg aaggtctgca cagattggga tatatcctgg   9120
aggagataga caagaaggat ggagacctaa tgtatgctga tgacacagca ggctgggaca   9180
caagaatcac tgaggatgac cttcaaaatg aggaactgat cacggaacag atggctcccc   9240
accacaagat cctagccaaa gccattttca aactaaccta tcaaaacaaa gtggtgaaag   9300
tcctcagacc cacaccgcgg ggagcggtga tggatatcat atccaggaaa gaccaaagag   9360
gtagtggaca agttggaaca tatggtttga acacattcac caacatggaa gttcaactca   9420
tccgccaaat ggaagctgaa ggagtcatca cacaagatga catgcagaac ccaaaagggt   9480
tgaaagaaag agttgagaaa tggctgaaag agtgtggtgt cgacaggtta aagaggatgg   9540
caatcagtgg agacgattgc gtggtgaagc cctagatga gaggtttgc acttccctcc   9600
tcttcttgaa cgacatggga aaggtgagga aagacattcc gcagtgggaa ccatctaagg   9660
gatgaaaaa ctgcaagag gttccttttt gctcccacca cttcacaag atctttatga    9720
aggatggccg ctcactagtt gttccatgta gaaaccagga tgaactgata gggagagcca   9780
gaatctcgca gggagctgga tggagcttaa gagaaacagc ctgcctgggc aaagcttacg   9840
```

```
cccagatgtg gtcgcttatg tacttccaca gaagggatct gcgtttagcc tccatggcca   9900
tatgctcagc agttccaacg gaatggtttc caacaagcag aacaacatgg tcaatccacg   9960
ctcatcacca gtggatgacc actgaagata tgctcaaagt gtggaacaga gtgtggatag  10020
aagacaaccc taatatgact gacaagactc cagtccattc gtgggaagat ataccttacc  10080
tagggaaaag agaggatttg tggtgtggat ccctgattgg actttcttcc agagccacct  10140
gggcgaagaa cattcacacg gccataaccc aggtcaggaa cctgatcgga aaagaggaat  10200
acgtggatta catgccagta atgaaaagat acagtgctcc ttcagagagt gaaggagttc  10260
tgtaattacc aacaacaaac accaaaggct attgaagtca ggccacttgt gccacggttt  10320
gagcaaaccg tgctgcctgt agctccgcca ataatgggag gcgtaataat ccccagggag  10380
gccatgcgcc acggaagctg tacgcgtggc atattggact agcggttaga ggagacccct  10440
cccatcactg acaaaacgca gcaaaagggg gcccaagact agaggttaga ggagaccccc  10500
ccaacacaaa aacagcatat tgacgctggg aaagaccaga gatcctgctg tctctgcaac  10560
atcaatccag gcacagagcn nnnnnnnnn nnnnnnnnnn nnnnnnnnnn nnnnnnnn    10618

<210> SEQ ID NO 3
<211> LENGTH: 10645
<212> TYPE: DNA
<213> ORGANISM: Dengue virus 3
<220> FEATURE:
<221> NAME/KEY: misc_feature
<222> LOCATION: (10644)..(10645)
<223> OTHER INFORMATION: n is a, c, g, or t

<400> SEQUENCE: 3
agttgttagt ctacgtggac cgacaagaac agtttcgact cggaagcttg cttaacgtag     60
tactgacagt ttttttattag agagcagatc tctgatgaac aaccaacgga aaaagacggg    120
aaaaccgtct atcaatatgc tgaaacgcgt gagaaaccgt gtgtcaactg gatcacagtt    180
ggcgaagaga ttctcaagag gactgctgaa cggccaagga ccaatgaaat tggttatggc    240
gttcatagct ttcctcagat ttctagccat tccaccgaca gcaggagtct tggctagatg    300
gggaaccttt aagaagtcgg gggctattaa ggtcctgaga ggcttcaaga aggagatctc    360
aaacatgctg agcattatca acagacggaa aaagacatcg ctctgtctca tgatgatgtt    420
accagcaaca cttgctttcc acttgacttc acgagatgga gagccgcgca tgattgtggg    480
gaagaatgaa agaggaaaat ccctactttt taagacagcc tctggaatca acatgtgcac    540
actcatagcc atggatttgg gagagatgtg tgatgacacg gtcacctaca atgcccccct    600
cattactgaa gtggagcctg aagacattga ctgctggtgc aaccttacat cgacatgggt    660
gacctacgga acgtgcaatc aagctggaga gcacagacgc gacaaaagat cggtggcgtt    720
agctccccat gtcggcatgg gactggacac acgcacccaa acctggatgt cggctgaagg    780
agcttggaga caggtcgaga aggtagagac atgggccttt aggcacccag ggttcacaat    840
actagcccta tttcttgccc attacatagg cacttccttg acccagaaag tggttatttt    900
catactacta atgctggtca ccccatccat gacaatgaga tgcgtgggag taggaaacag    960
agatttcgtg gaaggcctat caggagctac gtgggttgac gtggtgctcg agcacggtgg   1020
gtgtgtgact accatggcta agaacaagcc cacgctggat atagagctcc agaagaccga   1080
ggccacccaa ctggcgaccc taaggaaact atgtattgag ggaaaaatta ccaacgtaac   1140
aaccgactca aggtgcccca cccaagggga agcgatttta cctgaggagc aggaccagaa   1200
```

```
ccacgtgtgc aagcacacat acgtggacag aggctgggga acggttgtg gtttgtttgg      1260 caagggaagc ctggtaacat gcgcgaaatt tcaatgtttg gaatcaatag agggaaaagt      1320
ggtgcagcat gagaacctca aatacaccgt catcatcaca gtgcacacag gagatcaaca      1380
ccaggtggga aatgaaacgc agggagtcac ggctgagata caccccagg catcaaccgt       1440 tgaagccatc ttacctgaat atggaaccct tgggctagaa tgctcaccac ggacaggttt      1500
agatttcaat gaaatgattt tgttgacaat gaagaacaga gcatggatgg tacatagaca      1560
atggtttttt gacctacctt taccatggac atcaggagct acaacagaaa caccaacctg      1620
gaataagaaa gagcttcttg tgacattcaa aaacgcacat gcaaaaaagc aagaagtagt      1680
ggtccttgga tcgcaagagg gagcaatgca cacagcactg acaggagcta cagagatcca      1740
aacctcagga ggcacaagta tttttgcggg gcacttaaaa tgtagactca agatggacaa      1800
attggaactc aaggggatga gctatgcaat gtgcttgaat gcctttgtgt tgaagaaaga      1860
agtctccgaa acgcaacatg ggacaatact catcaaggtt gagtacaaag gggaagatgc      1920
accttgcaag attcctttct ccacggagga tggacaaggg aaagcccaca tggcagact      1980 gatcacagct aacccagtgg tgaccaagaa ggaggagcct gtcaatattg aggcagaacc      2040
tccttttggg gaaagcaata tagtaattgg aattggagac aaagccttga aaattaactg      2100
gtacaagaag ggaagctcga ttgggaagat gttcgaggcc actgccagag gtgcaaggcg      2160
catggccatc ttgggagaca cagcctggga ctttggatca gtaggggtg ttttaaattc       2220 attaggaaaa atggtgcacc aaatatttgg aagtgcttac acagccctat ttagtggagt      2280
ctcctggata atgaaaattg gaataggtgt cctttaacc tggataggt tgaattcaaa        2340 aaacactagt atgagcttta gctgcattgt gataggaatc attacactct atctgggagc      2400
cgtggtgcaa gctgacatgg ggtgtgtcat aaactgaaaa ggcaaagaac tcaaatgtgg      2460
aagtggaatt ttcgtcacta atgaggtcca cctggaca gagcaataca aatttcaagc        2520
agactccccc aaaagactgg cgacagccat tgcaggcgct tggagaatg gagtgtgcgg       2580 aatcaggtcg acaaccagaa tggagaacct cttgtggaag caaatagcca atgaactgaa      2640
ctacatatta tgggaaaaca acatcaaatt aacggtagtt gtgggtgata taattggggt      2700
cttagagcaa gggaaaagaa cactaacacc acaacccatg aactaaaat attcatggaa       2760 aacatgggga aaggcgaaga tagtgacagc tgaaacacaa aattcctctt tcataataga      2820
tgggccaaac acaccagagt gtccaagtgc ctcaagagca tggaatgtgt gggaggtgga      2880
agattacggt ttcggagtct tcacaactaa catatggctg aaactccgag agatgtacac      2940
ccaactatgt gaccacaggc taatgtcggc agccgttaag gatgagaggg ccgtacacgc      3000
cgacatgggc tattggatag aaagccaaaa gaatggaagt tggaagctag aaaaggcatc     3060
cctcatagag gtaaaaacct gcacatggcc aaaatcacac actctttgga gcaatggtgt     3120
gctagagagt gacatgatca tcccaaagag tctggctggt cccattcgc aacacaacta       3180 caggcccgga taccacaccc aaacggcagg accctggcac ttaggaaaat tggagctgga      3240
cttcaactat tgtgaaggaa caacagttgt catcacagaa aattgtggga caagaggccc      3300
atcactgaga caacaacag tgtcaggaa gttgatacac gaatggtgtt gccgctcgtg        3360
tacacttcct ccctgcgat acatgggaga agacggctgc tggtatggca tggaaattag       3420
acccattaat gagaaagaag agaacatggt aaagtcttta gtctcagcag ggagtggaaa     3480
ggtggataac ttcacaatgg gtgtcttgtg tttggcaatc ctttttgaag aggtgatgag      3540
aggaaaattt gggaaaaagc acatgattgc aggggttctc ttcacgtttg tactccttct     3600
```

```
ctcagggcaa ataacatgga gagacatggc gcacacactc ataatgattg ggtccaacgc    3660
ctctgacaga atgggaatgg gcgtcactta cctagcattg attgcaacat ttaaaattca    3720
gccatttttg gctttgggat tcttcctgag gaaactgaca tctagagaaa atttattgtt    3780
gggagttggg ttggccatgg caacaacgtt acaactgcca gaggacattg aacaaatggc    3840
gaatggaata gctttagggc tcatggctct taaattaata acacaatttg aaacatacca    3900
actatggacg gcattagtct ccctaatgtg ttcaaataca attttcacgt tgactgttgc    3960
ctggagaaca gccaccctga ttttggccgg aatttctctt ttgccagtgt gccagtcttc    4020
gagcatgagg aaaacagatt ggctcccaat ggctgtggca gctatgggag ttccacccct    4080 accactttt atttcagtt tgaaagatac gctcaaaagg agaagctggc cactgaatga    4140
gggggtgatg gctgttggac ttgtgagtat tctagctagt tctctcctta ggaatgacgt    4200
gcccatggct ggaccattag tggctggggg cttgctgata gcgtgctacg tcataactgg    4260
cacgtcagca gacctcactg tagaaaaagc agcagatgtg acatgggagg aagaggctga    4320
gcaaacagga gtgtcccaca atttaatgat cacagttgat gacgatggaa caatgagaat    4380
aaaagatgat gagactgaga acatcttaac agtgcttttg aaaacagcat tactaatagt    4440
gtcaggcatt tttccatact ccatacccgc aacactgttg gtctggcaca cttggcaaaa    4500
gcaaacccaa agatccggtg tcctatggga cgttcccagc cccccagaga cacagaaagc    4560
agaactggaa gaggggtttt ataggatcaa gcagcaagga attttggga aacccaagt    4620 gggggttgga gtacaaaaag aaggagtttt ccacaccatg tggcacgtca agaggagc    4680 agtgttgaca cacaatggga aaagactgga accaaactgg gctagcgtga aaaagatct    4740 gatttcatac ggaggaggat ggaaattgag tgcacaatgg caaaaggag aggaggtgca    4800 ggttattgcc gtagagcctg ggaagaaccc aaagaacttt caaaccatgc aggcattttt    4860
ccagacaaca acaggggaga taggagcgat tgcactggac ttcaagcctg aacttcagg    4920 atctcccatc ataaacagag agggaaaggt actgggattg tatggcaatg gagtggtcac    4980
aaagaatggt ggctatgtca gtggaatagc acaaacaaat gcagaaccag acggaccgac    5040
accagagttg gaagaagaga tgttcaaaaa gcgaaatcta accataatgg atctccatcc    5100
cgggtcagga aagacgcgga atatcttcc agctattgtt agagaggcaa tcaagagacg    5160
cttaaggact ctaattttgg caccaacaag ggtagttgca gctgagatgg aagaagcatt    5220
gaaagggctc ccaataaggt atcaaacaac tgcaacaaaa tctgaacaca gggagaga    5280 gattgttgat ctaatgtgcc acgcaacgtt cacaatgcgt ttgctgtcac cagtcagggt    5340
tccaaactac aacttgataa taatggatga ggctcatttc acagaccag ccagtatagc    5400 ggctagaggg tacatatcaa ctcgtgtagg aatgggagag gcagccgcaa ttttcatgac    5460
agccacaccc cctggaacag ctgatgcctt tcctcagagc aacgctccaa ttcaagatga    5520
agaaagagac ataccagaac gctcatggaa ttcaggcaat gaatgga ccgactttgc    5580 cgggaagacg gtgtggtttg tccctagcat caaagctgga aatgacatag caaactgctt    5640
gcggaaaaat ggaaaaaagg tcattcaact tagtaggaag acttttgaca cagaatatca    5700
aaagactaaa ctaaatgatt gggactttgt ggtgacaaca gacatttcag aaatgggagc    5760
caatttcaaa gcagacagag tgatcgaccc aagaagatgt ctcaagccag tgattttgac    5820
agacggaccc gagcgcgtga tcctggcggg accaatgcca gtcaccgtag cgagcgctgc    5880
gcaaaggaga gggagagttg gcaggaaccc acaaaaagaa aatgaccaat acatattcat    5940
```

```
gggccagccc ctcaataatg atgaagacca tgctcactgg acagaagcaa aaatgctgct    6000
agacaacatc aacacaccag aagggatcat accagctctc tttgaaccag aaagggagaa    6060
gtcagccgcc atagacggcg aataccgcct gaagggtgag tccaggaaga ccttcgtgga    6120
actcatgagg aggggtgacc tcccagtttg gctagcccat aaagtagcat cagaagggat    6180
caaatataca gatagaaagt ggtgttttga tggagaacgc aacaatcaaa ttttagagga    6240
gaatatggat gtggaaatct ggacaaagga aggagaaaag aaaaaattga gacctaggtg    6300
gcttgatgcc cgcacttatt cagatccctt agcgctcaag gaattcaagg actttgcggc    6360
tggtagaaag tcaattgccc ttgatcttgt gacagaaata ggaagagtgc cttcacactt    6420
agctcacaga acgagaaacg ccctggacaa tctggtgatg ttgcacacgt cagaacatgg    6480
cgggagggcc tacaggcatg cagtggagga actaccagaa acaatggaaa cactcttact    6540
cctgggactc atgatcctgt aacaggtgg agcaatgctt ttcttgatat caggtaaagg    6600
gattggaaag acttcaatag gactcatttg tgtagctgct tccagcggta tgttatggat    6660
ggctgatgtc ccactccaat ggatcgcgtc tgccatagtc ctggagtttt ttatgatggt    6720
gttacttata ccagaaccag aaaagcagag aactccccaa gacaatcaac tcgcatatgt    6780
cgtgataggc atactcacac tggctgcaat agtagcagcc aatgaaatgg gactgttgga    6840
aaccacaaag agagatttag gaatgtccaa agaaccaggt gttgtttctc aaccagcta     6900 tttggatgtg gacttgcacc cagcatcagc ctggacattg tacgctgtgg ccacaacagt    6960
aataacacca atgttgagac ataccataga gaattccaca gcaaatgtgt ccctggcagc    7020
tatagccaac caggcagtgg tcctgatggg tttagacaaa ggatggccga tatcgaaaat    7080
ggacttaggc gtgccactat tggcactggg ttgttattca caagtgaacc cactaactct    7140
cacagcggca gttctcctgc tagccacgca ttatgctatt ataggtccag attgcaggc    7200 aaaagccact cgtgaagctc aaaaaaggac agctgctgga ataatgaaga tccaacggt    7260 ggatgggata atgacaatag acctagatcc tgtaatatac gatccaaaat ttgaaaagca    7320
actaggacag gttatgctcc tggttctgtg tgcagttcaa ctttgttaa tgagaacatc    7380 atgggctttt tgtgaagctc taaccctagc cacaggacca ataacaacac tctgggaagg    7440
atcacctggg aagttctgga acaccacgat agctgtttcc atggcgaaca tctttagagg    7500
gagctattta gcaggagctg gcttgctttt ttctatcatg aaatcagttg aacaggaaa     7560 gagagggaca gggtcacagg gtgaaacctt gggagaaaag tggaaaagaa aattgaatca    7620
attaccccgg aaagagtttg acctttacaa gaaatccgga atcactgaag tggatagaac    7680
agaagccaaa gaagggttga aaagaggaga ataacacac catgccgtgt ccagaggcag    7740
cgcaaaactt caatggttcg tggagagaaa catggtcatc cccgaaggaa gagtcataga    7800
cttaggctgt ggaagaggag gctggtcata ttattgtgca ggactgaaaa aagttacaga    7860
agtgcgagga tacacaaaag gcggcccagg acatgaagaa ccagtaccta tgtctacata    7920
cggatggaac atagtcaagt taatgagtgg aaaggatgtg tttatcttc cacctgaaaa    7980 gtgtgatact ctattgtgtg acattggaga atcttcacca agcccaacag tggaagaaag    8040
cagaaccata gagtcttga agatggttga accatggcta agaaataacc agttttgcat    8100
taaagtattg aacccttaca tgccaactgt gattgagcac ctagaaagac tacaaggaa     8160 acatggagga atgcttgtga gaatccact ctcacgaaac tccacgcacg aaatgtactg     8220
gatatctaat ggcacaggca atatcgtttc ttcagtcaac atggtatcca gattgctact    8280
taacagattc acaatgacac ataggagacc caccatagag aaagatgtgg atttaggagc    8340
```

```
ggggacccga catgtcaatg cggaaccaga acacccaac atggatgtca ttggggaaag      8400
aataagaagg atcaaggagg agcatagttc aacatggcac tatgatgatg aaaatcctta    8460
taaaacgtgg gcttaccatg gatcctatga agttaaggcc acaggctcag cctcctccat    8520
gataaatgga gtcgtgaaac tcctcacgaa accatgggat gtggtgccca tggtgacaca    8580
gatggcaatg acggatacaa ccccattcgg ccagcaaagg gtttttaaag agaaagtgga    8640
caccaggaca cccagaccta tgccaggaac aagaaaggtt atggagatca cagcggaatg    8700
gctttggaga accctgggaa ggaacaaaag acccagatta tgtacgagag aggagttcac    8760
aaaaaaggtc agaaccaacg cagctatggg cgccgttttt acagaggaga accaatggga    8820
cagtgctaga gctgctgttg aggatgaaga attctggaaa ctcgtggaca gagaacgtga    8880
actccacaaa ttgggcaagt gtggaagctg cgtttacaac atgatgggca agagagagaa    8940
gaaacttgga gagtttggca agcaaaagg cagtagagcc atatggtaca tgtggttggg    9000
agccagatac cttgagttcg aagcactcgg attcttaaat gaagaccatt ggttctcgcg    9060
tgaaaactct tacagtggag tagaaggaga aggactgcac aagctgggat acatcttaag    9120
agacatttcc aagatacccg gaggagctat gtatgctgat gacacagctg gttgggacac    9180
aagaataaca gaagatgacc tgcacaatga ggaaaaaatc acacagcaaa tggaccctga    9240
acacaggcag ttagcaaacg ctatattcaa gctcacatac caaaacaaag tggtcaaagt    9300
tcaacgacca actccaaagg gcacggtaat ggacatcata tctaggaaag accaaagagg    9360
cagtggacag gtgggaactt atggtctgaa tacattcacc aacatggaag cccagttaat    9420
cagacaaatg gaaggagaag gtgtgttgtc gaaggcagac ctcgagaacc ctcatctgct    9480
agagaagaaa gttacacaat ggttggaaac aaaaggagtg gagaggttaa aagaatggc    9540
catcagcggg gatgattgcg tggtgaaacc aattgatgac aggttcgcca atgccctgct    9600
tgccctgaat gacatgggaa aagttaggaa ggacatacct caatggcagc catcaaaggg    9660
atggcatgat tggcaacagg tcccttctg ctcccaccac tttcatgaat tgatcatgaa    9720
agatggaaga aagttggtag ttccctgcag acctcaggat gaattaatcg ggagagcgag    9780
aatctctcaa ggagcaggat ggagccttag agaaactgca tgcctaggga aagcctacgc    9840
ccaaatgtgg actctcatgt actttcacag aagagatctt agactagcat ccaacgccat    9900
atgttcagca gtaccagtcc attgggtccc cacaagcaga acgacgtggt ctattcatgc    9960
tcaccatcag tggatgacta cagaagacat gcttactgtt tggaacaggg tgtggataga   10020
ggataatcca tggatggaag acaaaactcc agtcaaaacc tgggaagatg ttccatatct   10080
agggaagaga gaagaccaat ggtgcggatc actcattggt ctcacttcca gagcaacctg   10140
ggcccagaac atacttacgg caatccaaca ggtgagaagc cttataggca atgaagagtt   10200
tctggactac atgccttcga tgaagagatt caggaaggag gaggagtcag agggagccat   10260
ttggtaaacg taggaagtga aaagaggca aactgtcagg ccaccttaag ccacagtacg   10320
gaagaagctg tgcagcctgt gagccccgtc aaggacgtt aaaagaagaa gtcaggccca   10380
aaagccacgg tttgagcaaa ccgtgctgcc tgtggctccg tcgtggggac gtaaaacctg   10440
ggaggctgcg actagcggtt agaggagacc cctcccgtga cacaacgcag cagcggggcc   10500
caagactaga ggttagagga gaccccccgc aaataaaaac agcatattga cgctgggaga   10560
gaccagagat cctgctgtct cctcagcatc attccaggca cagaacgcca gaaaatggaa   10620
tggtgctgtt gaatcaacag gttnn                                         10645
```

<210> SEQ ID NO 4
<211> LENGTH: 10618
<212> TYPE: DNA
<213> ORGANISM: Dengue virus 4
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: misc_feature
<222> LOCATION: (10579)..(10618)
<223> OTHER INFORMATION: n is a, c, g, or t

<400> SEQUENCE: 4

```
nnnnnnnnnn nnnnnnggac cgacaaggac agttccaaat cggaagcttg cttaacacag     60
ttctaacagt ttgtttgaat agagagcaga tctctggaaa aatgaaccaa cgaaaaaagg    120
tggttagacc acctttcaat atgctgaaac gcgagagaaa ccgcgtatca acccctcaag    180
ggttggtgaa gagattctca accggacttt tttctgggaa aggaccctta cggatggtgc    240
tagcattcat cacgtttttg cgagtccttt ccatcccacc aacagcaggg attctgaaga    300
gatggggaca gttgaagaaa aataaggcca tcaagatact gattggattc aggaaggaga    360
taggccgcat gctgaacatc ttgaacggga gaaaaaggtc aacgataaca ttgctgtgct    420
tgattcccac cgtaatggcg ttttccctca gcacaagaga tggcgaaccc ctcatgatag    480
tggcaaaaca tgaaaggggg agacctctct tgtttaagac aacagagggg atcaacaaat    540
gcactctcat tgccatggac ttgggtgaaa tgtgtgagga cactgtcacg tataaatgcc    600
ccctactggt caataccgaa cctgaagaca ttgattgctg gtgcaacctc acgtctacct    660
gggtcatgta tgggacatgc acccagagcg gagaacggag acgagagaag cgctcagtag    720
ctttaacacc acattcagga atgggattgg aaacaagagc tgagacatgg atgtcatcgg    780
aaggggcttg gaagcatgct cagagagtag agagctggat actcagaaac ccaggattcg    840
cgctcttggc aggatttatg gcttatatga ttgggcaaac aggaatccag cgaactgtct    900
tctttgtcct aatgatgctg gtcgccccat cctacggaat gcgatgcgta ggagtaggaa    960
acagagactt tgtggaagga gtctcaggtg gagcatgggt cgacctggtg ctagaacatg   1020
gaggatgcgt cacaaccatg gcccagggaa aaccaacctt ggattttgaa ctgactaaga   1080
caacagccaa ggaagtggct ctgttaagaa cctattgcat tgaagcctca atatcaaaca   1140
taactacggc aacaagatgt ccaacgcaag gagagcctta tctgaaagag gaacaggacc   1200
aacagtacat ttgccggaga gatgtggtag acagagggtg gggcaatggc tgtggcttgt   1260
ttggaaaagg aggagttgtg acatgtgcga agttttcatg ttcggggaag ataacaggca   1320
atttggtcca aattgagaac cttgaataca cagtggttgt aacagtccac aatggagaca   1380
cccatgcagt aggaaatgac acatccaatc atggagttac agccatgata actcccaggt   1440
caccatcggt ggaagtcaaa ttgccggact atggagaact aacactcgat tgtgaaccca   1500
ggtctggaat tgactttaat gagatgattc tgatgaaaat gaaaaagaaa acatggctcg   1560
tgcataagca atggtttttg gatctgcctc ttccatggac agcaggagca gacacatcag   1620
aggttcactg gaattacaaa gagagaatgg tgacatttaa ggttcctcat gccaagagac   1680
aggatgtgac agtgctggga tctcaggaag gagccatgca ttctgccctc gctggagcca   1740
cagaagtgga ctccggtgat ggaaatcaca tgtttgcagg acatcttaag tgcaaagtcc   1800
gtatggagaa attgagaatc aagggaatgt catacacgat gtgttcagga aagttttcaa   1860
ttgacaaaga gatggcagaa acacagcatg ggacaacagt ggtgaaagtc aagtatgaag   1920
```

```
gtgctggagc tccgtgtaaa gtccccatag agataagaga tgtaaacaag gaaaaagtgg    1980
ttgggcgtat catctcatcc accccttttgg ctgagaatac caacagtgta accaacatag   2040
aattagaacc ccccctttggg gacagctaca tagtgatagg tgttggaaac agcgcattaa   2100
cactccattg gttcaggaaa gggagttcca ttggcaagat gtttgagtcc acatacagag   2160
gtgcaaaacg aatggccatt ctaggtgaaa cagcttggga ttttggttcc gttggtggac   2220
tgttcacatc attgggaaag gctgtgcacc aggttttttgg aagtgtgtat acaaccatgt  2280
ttggaggagt ctcatggatg attagaatcc taattgggtt cttagtgttg tggattggca   2340
cgaactcgag gaacacttca atggctatga cgtgcatagc tgttggagga atcactctgt   2400
ttctgggctt cacagttcaa gcagacatgg gttgtgtggc gtcatggagt gggaaagaat   2460
tgaagtgtgg aagcggaatt tttgtggttg acaacgtgca cacttggaca gaacagtaca   2520
aatttcaacc agagtcccca gcgagactag cgtctgcaat attaaatgcc cacaaagatg   2580
gggtctgtgg aattagatca accacgaggc tggaaaatgt catgtggaag caaataacca   2640
acgagctaaa ctatgttctc tgggaaggag gacatgacct cactgtagtg gctggggatg   2700
tgaagggggt gttgaccaaa ggcaagagag cactcacacc cccagtgagt gatctgaaat   2760
attcatggaa gacatgggga aaagcaaaaa tcttcacccc agaagcaaga aatagcacat   2820
ttttaataga cggaccagac acctctgaat gccccaatga acgaagagca tggaactctc   2880
ttgaggtgga agactatgga tttggcatgt tcacgaccaa catatggatg aaattccgag   2940
aaggaagttc agaagtgtgt gaccacaggt taatgtcagc tgcaattaaa gatcagaaag   3000
ctgtgcatgc tgacatgggt tattggatag agagctcaaa aaaccagacc tggcagatag   3060
agaaagcatc tcttattgaa gtgaaaacat gtctgtggcc caagacccac acactgtgga   3120
gcaatggagt gctggaaagc cagatgctca ttccaaaatc atatgcgggc cctttttcac   3180
agcacaatta ccgccagggc tatgccacgc aaaccgtggg cccatggcac ttaggcaaat   3240
tagagataga cttttgagaa tgccccggaa caacagtcac aattcaggag gattgtgacc   3300
atagaggccc atctttgagg accaccactg catctggaaa actagtcacg caatggtgct   3360
gccgctcctg cacgatgcct cccttaaggt tcttgggaga gatgggtgc tggtatggga   3420 tggagattag gcccttgagt gaaaagaag agaacatggt caaatcacag gtgacggccg   3480
gacagggcac atcagaaact ttttctatgg gtctgttgtg cctgacctttg tttgtggaag  3540 aatgcttgag gagaagagtc actaggaaac acatgatatt agttgtggtg atcactcttt   3600
gtgctatcat cctgggaggc ctcacatgga tggacttact acgagccctc atcatgttgg   3660
gggacactat gtctggtaga ataggaggac agatccacct agccatcatg gcagtgttca   3720
agatgtcacc aggatacgtg ctgggtgtgt ttttaaggaa actcacttca agagagacag   3780
cactaatggt aataggaatg gccatgacaa cggtgctttc aattccacat gaccttatgg   3840
aactcattga tggaatatca ctgggactaa ttttgctaaa aatagtaaca cagtttttgaca  3900 acacccaagt gggaaccttag ctctttcct tgactttcat aagatcaaca atgccattgg   3960
tcatggcttg gaggaccatt atggctgtgt tgtttgtggt cacactcatt cctttgtgca   4020
ggacaagctg tcttcaaaaa cagtctcatt gggtagaaat aacagcactc atcctaggag   4080
cccaagctct gccagtgtac ctaatgactc ttatgaaagg agcctcaaga agatcttggc   4140
ctcttaacga gggcataatg gctgtggggt tggttagtct cttaggaagc gctcttttaa   4200
agaatgatgt ccccttagct ggcccaatgg tggcaggagg cttacttctg gcggcttacg   4260
```

```
tgatgagtgg tagctcagca gatctgtcac tagagaaggc cgccaacgtg cagtgggatg    4320
aaatggcaga cataacaggc tcaagcccaa tcatagaagt gaagcaggat gaagatggct    4380 cttttctccat acgggacgtc gaggaaacca atatgataac ccttttggtg aaactggcac    4440
tgataacagt gtcaggtctc tacccctggg caattccagt cacaatgacc ttatggtaca    4500
tgtggcaagt gaaaacacaa agatcaggag ccctgtggga cgtcccctca cccgctgcca    4560 ctaaaaagc cgcactgtct gaaggagtgt acaggatcat gcaaagaggg ttattcggga    4620
aaactcaggt tggagtaggg atacacatgg aaggtgtatt tcacacaatg tggcatgtaa    4680
caagaggatc agtgatctgc cacgagactg ggagattgga gccatcttgg gctgacgtca    4740
ggaatgacat gatatcatac ggtgggggat ggaggcttgg agacaaatgg gacaaagaag    4800
aagacgttca ggtcctcgcc atagaaccag gaaaaaatcc taaacatgtc caaacgaaac    4860
ctggcctttt caagacccta actggagaaa ttggagcagt aacattagat ttcaaacccg    4920
gaacgtctgg ttctcccatc atcaacagga aggaaaagt catcggactc tatggaaatg    4980
gagtagttac caaatcaggt gattacgtca gtgccataac gcaagccgaa agaattggag    5040
agccagatta tgaagtggat gaggacattt ttcgaaagaa aagattaact ataatggact    5100 tacacccgg agctggaaag acaaaaagaa ttcttccatc aatagtgaga gaagccttaa    5160
aaaggaggct acgaactttg attttagctc ccacgagagt ggtggcggcc gagatggaag    5220
aggccctacg tggactgcca atccgttatc agacccagc tgtgaaatca aacacacag    5280 gaagagagat tgtagacctc atgtgtcatg caaccttcac aacaagactt tgtcatcaa    5340 ccagggttcc aaattacaac cttatagtga tggatgaagc acatttcacc gatccttcta    5400
gtgtcgcggc tagaggatac atctcgacca gggtggaaat gggagaggca gcagccatct    5460
tcatgaccgc aacccctccc ggagcgacag atccctttcc ccagagcaac agcccaatag    5520
aagacatcga gagggaaatt ccggaaaggt catggaacac agggttcgac tggataacag    5580
actaccaagg gaaaactgtg tggtttgttc ccagcataaa agctggaaat gacattgcaa    5640
attgtttgag aaagtcggga aagaaagtta tccagttgag taggaaaacc tttgatacag    5700
agtatccaaa aacgaaactc acggactggg acttttgtgt cactacagac atatctgaaa    5760
tgggggccaa tttttagagcc gggagagtga tagaccctag aagatgcctc aagccagtta    5820
tcctaccaga tgggccagag agagtcattt tagcaggtcc tattccagtg actccagcaa    5880
gcgctgctca gagaagaggg cgaataggaa ggaacccagc acaagaagac gaccaatacg    5940
ttttctccgg agacccacta aaaaatgatg aagatcatgc ccactggaca gaagcaaaga    6000
tgctgcttga caatatctac acccccagaag ggatcattcc aacattgttt ggtccggaaa    6060
gggaaaaaac ccaagccatt gatggagagt ttcgcctcag aggggaacaa aggaagactt    6120 tgtggaatt aatgaggaga ggagaccttc cggtgtggct gagctataag gtagcttctg    6180
ctggcatttc ttacaaagat cgggaatggt gcttcacagg ggaaagaaat aaccaaattt    6240
tagaagaaaa catggaggtt gaaatttgga ctagagaggg agaaaagaaa aagctaaggc    6300
caagatggtt agatgcacgt gtatacgctg accccatggc tttgaaggat ttcaaggagt    6360
ttgccagtgg aagaagagt ataactctcg acatcctaac agagattgcc agtttgccaa    6420
cttacctttc ctctagggcc aagctcgccc ttgataacat agtcatgctc cacacaacag    6480
aaagaggagg gagggcctat caacacgccc tgaacgaact tccggagtca ctggaaacac    6540
tcatgcttgt agctttacta ggtgctatga cagcaggcat cttcctgttt ttcatgcaag    6600
ggaaaggaat agggaaattg tcaatggggt tgataaccat tgcggtggct agtggcttgc    6660
```

```
tctgggtagc agaaattcaa ccccagtgga tagcggcctc aatcatacta gagttttttc    6720
tcatggtact gttgataccg gaaccagaaa aacaaaggac cccacaagac aatcaattga    6780
tctacgtcat attgaccatt ctcaccatca ttggtctaat agcagccaac gagatggggc    6840
tgattgaaaa aacaaaaacg gattttgggt tttaccaggt aaaaacagaa accaccatcc    6900
tcgatgtgga cttgagacca gcttcagcat ggacgctcta tgcagtagcc accacaattc    6960
tgactcccat gctgagacac accatagaaa acacgtcggc caacctatct ctagcagcca    7020
ttgccaacca ggcagccgtc ctaatggggc ttggaaaagg atggccgctc cacagaatgg    7080
acctcggtgt gccgctgtta gcaatgggat gctattctca agtgaaccca ataaccttga    7140
cagcatcctt agtcatgctt ttcgtccatt atgcaataat aggcccagga ttgcaggcaa    7200
aagccacaag agaggcccag aaaaggacag ctgctgggat catgaaaaat cccacagtgg    7260
acgggataac agtaatagat ctagaaccaa tatcctatga cccaaaattt gaaaagcaat    7320
tagggcaggt catgctacta gtcttgtgtg ctggacaact actcttgatg agaacaacat    7380
gggctttctg tgaagtcttg actttggcca caggaccaat cttgaccttg tgggagggca    7440
acccgggaag gttttggaac acgaccatag ccgtatccac cgccaacatt ttcaggggaa    7500
gttacttggc gggagctgga ctggcttttt cactcataaa gaatgcacaa cccctagga    7560 ggggaactgg gaccacagga gagacactgg gagagaagtg gaagagacag ctaaactcat    7620
tagacagaaa agagtttgaa gagtataaaa gaagtggaat actagaagtg gacaggactg    7680
aagccaagtc tgccctgaaa gatgggtcta aaatcaagca tgcagtatca agagggtcca    7740
gtaagatcag atggattgtt gagagaggga tggtaaagcc aaaagggaaa gttgtagatc    7800
ttggctgtgg gagaggagga tggtcttatt acatggcgac actcaagaac gtgactgaag    7860
tgaaagggta tacaaaagga ggtccaggac atgaagaacc gattcccatg gctacttatg    7920
gttggaattt ggtcaaactc cattcagggg ttgacgtgtt ctacaaaccc acagagcaag    7980
tggacaccct gctctgtgat attggggagt catcttctaa tccaacaata gaggaaggaa    8040
gaacattaag agttttgaag atggtggagc catggctctc ttcaaaacct gaattctgca    8100
tcaaagtcct taacccctac atgccaacag tcatagaaga gctggagaaa ctgcagagaa    8160
aacatggtgg gaaccttgtc agatgcccgc tgtccaggaa ctccaccat gagatgtatt    8220 gggtgtcagg agcgtcggga aacattgtga gctctgtgaa cacaacatca aagatgttgt    8280
tgaacaggtt cacaacaagg cataggagac ctacttatga aaggacgta gatcttgggg    8340 caggaacgag aagtgtctcc actgaaacag aaaaaccaga catgacaatc attgggagaa    8400
ggcttcagcg attgcaagaa gagcacaaag aaacctggca ttatgatcag gaaaacccat    8460
acagaacctg gcgtatcat ggaagctatg aagctccttc gacaggctct gcatcctcca    8520
tggtgaacgg ggtggtaaaa ctgctaacaa acccctggga tgtgattcca atggtgactc    8580
agttagccat gacagataca accccttttg gcaacaaag agtgttcaaa gagaaggtgg    8640
ataccagaac accacaacca aaacccggta cacgaatggt tatgaccacg acagccaatt    8700
ggctgtgggc cctccttgga aagaagaaaa atcccagact gtgcacaagg gaagagttca    8760
tctcaaaagt tagatcaaac gcagccatag gcgcagtctt tcaggaagaa caggatggaa    8820
catcagccag tgaagctgtg aatgacagcc ggttttggga actggttgac aaagaagggg    8880
ccctacacca ggaagggaaa tgtgaatcgt gtgtctataa catgatggga aaacgtgaga    8940
aaaagttagg agagtttggc agagccaagg gaagccgagc aatctggtac atgtggctgg    9000
```

```
gagcgcggtt tctggaattt gaagccctgg gttttttgaa tgaagatcac tggtttggca    9060
gagaaaattc atggagtgga gtggaagggg aaggtctgca cagattggga tatatcctgg    9120
aggagataga caagaaggat ggagacctaa tgtatgctga tgacacagca ggctgggaca    9180
caagaatcac tgaggatgac cttcaaaatg aggaactgat cacggaacag atggctcccc    9240
accacaagat cctagccaaa gccattttca aactaaccta tcaaaacaaa gtggtgaaag    9300
tcctcagacc cacaccgcgg ggagcggtga tggatatcat atccaggaaa gaccaaagag    9360
gtagtggaca agttggaaca tatggtttga acacattcac caacatggaa gttcaactca    9420
tccgccaaat ggaagctgaa ggagtcatca cacaagatga catgcagaac ccaaaagggt    9480
tgaaagaaag agttgagaaa tggctgaaag agtgtggtgt cgacaggtta aagaggatgg    9540
caatcagtgg agacgattgc gtggtgaagc ccctagatga gaggtttggc acttccctcc    9600
tcttcttgaa cgacatggga aaggtgagga agacattcc gcagtgggaa ccatctaagg    9660
gatggaaaaa ctggcaagag gttcctttt gctcccacca ctttcacaag atctttatga    9720
aggatggccg ctcactagtt gttccatgta gaaaccagga tgaactgata gggagagcca    9780
gaatctcgca gggagctgga tggagcttaa gagaaacagc ctgcctgggc aaagcttacg    9840
cccagatgtg gtcgcttatg tacttccaca agagggatct gcgtttagcc tccatggcca    9900
tatgctcagc agttccaacg gaatggtttc caacaagcag aacaacatgg tcaatccacg    9960
ctcatcacca gtggatgacc actgaagata tgctcaaagt gtggaacaga gtgtggatag   10020
aagacaaccc taatatgact gacaagactc cagtccattc gtgggaagat atacctacc    10080 tagggaaaag agaggatttg tggtgtggat ccctgattgg actttcttcc agagccacct   10140
gggcgaagaa cattcacacg gccataaccc aggtcaggaa cctgatcgga aaagaggaat   10200
acgtggatta catgccagta atgaaaagat acagtgctcc ttcagagagt gaaggagttc   10260
tgtaattacc aacaacaaac accaaaggct attgaagtca ggccacttgt gccacggttt   10320
gagcaaaccg tgctgcctgt agctccgcca ataatgggag cgtaataat ccccaggag     10380 gccatgcgcc acggaagctg tacgcgtggc atattggact agcggttaga ggagacccct   10440
cccatcactg acaaaacgca gcaaaagggg cccaagact agaggttaga ggagaccccc    10500
ccaacacaaa aacagcatat tgacgctggg aaagaccaga gatcctgctg tctctgcaac   10560
atcaatccag gcacagagnn nnnnnnnnnn nnnnnnnnnn nnnnnnnnnn nnnnnnnn     10618
```